(12) United States Patent
Smith et al.

(10) Patent No.: US 11,684,768 B2
(45) Date of Patent: Jun. 27, 2023

(54) BLOOD PUMP ASSEMBLY AND METHOD OF USE THEREOF

(71) Applicant: NuPulseCV, Inc., Raleigh, NC (US)

(72) Inventors: Robert M. Smith, Raleigh, NC (US); Valluvan Jeevanandam, Raleigh, NC (US)

(73) Assignee: NuPulseCV, Inc., Raleigh, NC (US)

( * ) Notice: Subject to any disclaimer, the term of this patent is extended or adjusted under 35 U.S.C. 154(b) by 0 days.

(21) Appl. No.: 15/685,553

(22) Filed: Aug. 24, 2017

(65) Prior Publication Data

US 2018/0055981 A1    Mar. 1, 2018

Related U.S. Application Data

(60) Provisional application No. 62/379,032, filed on Aug. 24, 2016.

(51) Int. Cl.
| | | |
|---|---|---|
| *A61M 60/148* | (2021.01) | |
| *A61M 60/139* | (2021.01) | |
| *A61M 60/865* | (2021.01) | |
| *A61M 60/867* | (2021.01) | |
| *A61M 60/843* | (2021.01) | |
| *A61M 60/295* | (2021.01) | |
| *A61M 60/497* | (2021.01) | |
| *A61M 60/861* | (2021.01) | |

(52) U.S. Cl.
CPC ........ *A61M 60/148* (2021.01); *A61M 60/139* (2021.01); *A61M 60/295* (2021.01); *A61M 60/497* (2021.01); *A61M 60/843* (2021.01); *A61M 60/861* (2021.01); *A61M 60/865* (2021.01); *A61M 60/867* (2021.01)

(58) Field of Classification Search
CPC .... A61M 1/122; A61M 1/106; A61M 1/1072; A61M 1/127; A61M 1/1008; A61M 1/101; A61M 1/125; A61M 60/148; A61M 60/139; A61M 60/295; A61M 60/497; A61M 60/843; A61M 60/861; A61M 60/865; A61M 60/867
See application file for complete search history.

(56) References Cited

U.S. PATENT DOCUMENTS

| | | |
|---|---|---|
| 3,964,470 A | 6/1976 | Trombley |
| 4,038,625 A | 7/1977 | Tompkins et al. |
| 4,276,874 A * | 7/1981 | Wolvek ............ A61M 25/0054 600/18 |

(Continued)

FOREIGN PATENT DOCUMENTS

| | | |
|---|---|---|
| DE | 3722161 A1 | 1/1998 |
| EP | 0228787 A1 | 7/1987 |

(Continued)

OTHER PUBLICATIONS

BioSpan: "*Segmented Polyurethane (SPU)*". www.dsm.com, DSM, 2014. www.dsm.com/markets/medical/en_US/products-page/products-biostable-Polyurethanes/product-pu-biospan-spu.htm; 2 pages.

(Continued)

*Primary Examiner* — Mallika D Fairchild
(74) *Attorney, Agent, or Firm* — Loeb & Loeb LLP

(57) ABSTRACT

The invention provides a blood pump for use with an intravascular ventricular assist system (iVAS), as well as a method for utilizing the blood pump to treat heart failure.

49 Claims, 24 Drawing Sheets

(56) References Cited

U.S. PATENT DOCUMENTS

| | | | |
|---|---|---|---|
| 4,327,709 A * | 5/1982 | Hanson | A61M 60/859 |
| | | | 604/914 |
| 5,098,397 A | 3/1992 | Svensson et al. | |
| 5,176,619 A * | 1/1993 | Segalowitz | A61M 60/569 |
| | | | 600/16 |
| 5,350,413 A | 9/1994 | Miller | |
| 5,782,645 A | 7/1998 | Stobie et al. | |
| 5,817,001 A * | 10/1998 | Leschinsky | A61M 60/43 |
| | | | 600/18 |
| 5,904,646 A | 5/1999 | Jarvik | |
| 6,453,195 B1 | 9/2002 | Thompson | |
| 6,530,876 B1 | 3/2003 | Spence | |
| 7,632,263 B2 | 12/2009 | Denoth et al. | |
| 7,666,167 B2 | 2/2010 | Bierman | |
| 7,766,881 B2 | 8/2010 | Reinmann | |
| 7,892,162 B1 | 2/2011 | Jeevanandam et al. | |
| 7,935,096 B2 | 5/2011 | Johansson et al. | |
| 7,988,674 B2 | 8/2011 | Adams et al. | |
| 8,066,628 B1 * | 11/2011 | Jeevanandam | A61M 60/135 |
| | | | 600/17 |
| 8,152,769 B2 | 4/2012 | Douglas et al. | |
| 8,323,174 B2 | 12/2012 | Jeevanandam et al. | |
| 8,574,204 B2 | 11/2013 | Bourne et al. | |
| 9,125,981 B2 | 9/2015 | Mann et al. | |
| 9,265,871 B2 | 2/2016 | Jeevanandam et al. | |
| 9,592,328 B2 | 3/2017 | Jeevanandam et al. | |
| 10,137,230 B2 | 11/2018 | Novack | |
| 2002/0077600 A1 * | 6/2002 | Sirimanne | A61M 25/0606 |
| | | | 606/198 |
| 2003/0074144 A1 | 4/2003 | Freed et al. | |
| 2004/0152945 A1 * | 8/2004 | Kantrowitz | A61M 60/135 |
| | | | 600/18 |
| 2004/0249361 A1 | 12/2004 | Denoth et al. | |
| 2006/0271091 A1 * | 11/2006 | Campbell | A61M 25/104 |
| | | | 606/192 |
| 2007/0191779 A1 | 8/2007 | Shubayev et al. | |
| 2008/0183136 A1 * | 7/2008 | Lenker | A61M 25/0662 |
| | | | 604/164.03 |
| 2012/0108885 A1 | 5/2012 | Jeevanandam et al. | |
| 2012/0149970 A1 | 6/2012 | Jeevanandam et al. | |
| 2013/0066365 A1 | 3/2013 | Belson et al. | |
| 2013/0331638 A1 | 12/2013 | Cameron et al. | |
| 2015/0157842 A1 | 6/2015 | Gill et al. | |
| 2015/0258261 A1 | 9/2015 | Novack | |
| 2016/0136343 A1 | 5/2016 | Anagnostopoulos | |

FOREIGN PATENT DOCUMENTS

| | | |
|---|---|---|
| GB | 2050175 A | 8/1980 |
| JP | H09122243 | 5/1997 |
| JP | 2013508094 | 3/2013 |
| JP | 6297484 | 3/2018 |
| WO | 91/11208 A1 | 8/1991 |
| WO | 2011050279 | 4/2011 |
| WO | 2012101267 A1 | 8/2012 |

OTHER PUBLICATIONS

International Search Report dated Nov. 9, 2017, regarding PCT/US2017/048429.

USPTO, International Search Report and Written Opinion for International Patent Application No. PCT/US17/48429. dated Nov. 9, 2017. 21 pages.

EPO, Extended European Search Report dated Feb. 18, 2020 for European Patent Application No. 17844423.8. 7 pages.

EPO, Supplemental European Search Report for European Patent Application No. 15765631.5. dated Oct. 26, 2017. 7 pages.

EPO, Examination Report for European Patent Application No. 15765631.5. dated Oct. 1, 2019. 4 pages.

Jeevanandam et al. "Circulatory Assistance with a Permanent Implantable IABP: Initial Human Experience" Circulation, 2002, 106:I-183-I-188.

Kantrowitz et al. "A Mechanical Auxiliary Ventricle: Histologic Responses to Long-Term, Intermittent Pumping in Calves" ASAIO Journal, 1995, 41(34), M340-M345.

Li et al. "The Kantrowitz Cardiovad™ System Can Be Deactivated For Two Months and Reactivated Without Thromboembolism" ASAIO Journal, 2000, vol. 46, No. 2, p. 205.

USPTO, International Search Report and Written Opinion for International Patent Application No. PCT/US2014/053943. dated Jan. 23, 2015. 9 pages.

USPTO, International Search Report and Written Opinion for International Patent Application No. PCT/US2015/020803. dated Jun. 25, 2015. 14 pages.

European Patent Office Communication pursuant to Article 94(3) EPC for App. No. EP17844423.8, dated Oct. 22, 2021, 5 pages.

Japanese Office Action (with English translation) for App. No. JP2019-510708, dated Jul. 9, 2021, 10 pages.

* cited by examiner

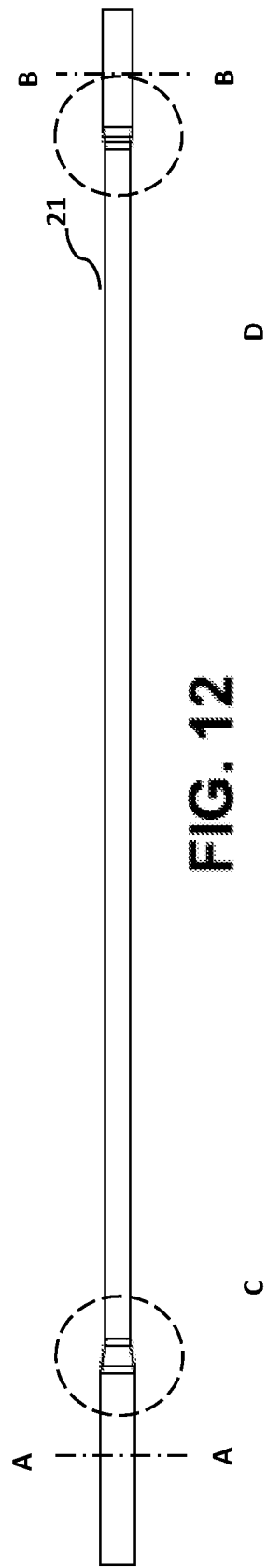
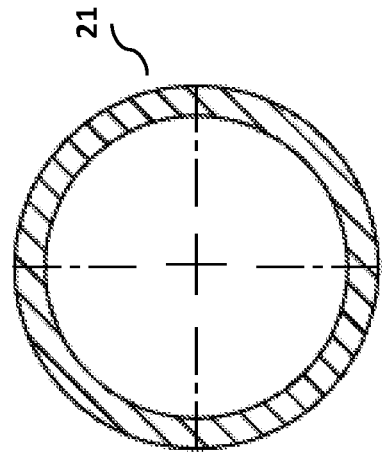
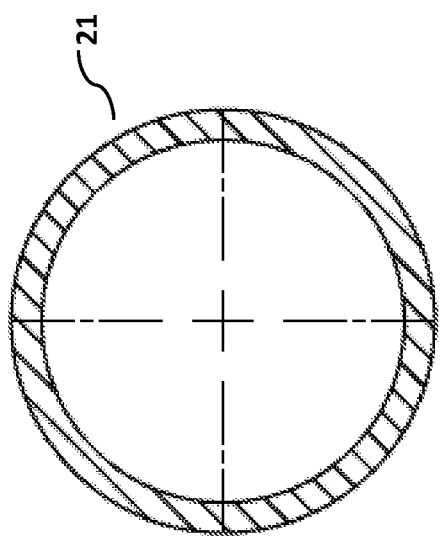
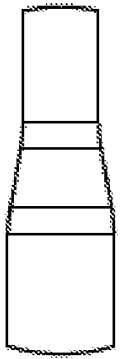
FIG. 12
FIG. 13
FIG. 14
FIG. 15
FIG. 16

BLOOD PUMP ASSEMBLY AND METHOD OF USE THEREOF

CROSS-REFERENCE TO RELATED APPLICATIONS

This application claims benefit of priority under 35 U.S.C. § 119(e) of U.S. Patent Application Ser. No. 62/379,032, filed Aug. 24, 2016, the entire contents of which is incorporated herein by reference in its entirety.

BACKGROUND OF THE INVENTION

Field of the Invention

The invention relates generally to a cardiac assist device (CAD) and more particularly to a blood pump suitable for use with a CAD, as well as a method for treating a subject with the blood pump.

Background Information

The use of CADs is a well known method for treating heart failure. A blood pump is positioned inside the aorta, typically in the proximal descending aorta. The pump typically comprises a displacement volume of 40-50 cc, and works in series with the heart to augment blood flow. During diastole, the pump is inflated, thereby driving blood in the ascending aorta and aortic arch into the coronary arteries to supply oxygen to the heart muscle. During systole, as the left ventricle contracts, the pump is deflated so as to decrease the afterload.

While the use of the blood pump portion of a CAD is well known, a number of complications have been evidenced during use of conventional blood pumps. One potentially serious complication arises from excessive blockage of the aorta during systole when the pump is in a delated state due to the inability of conventional pumps to maintain a deflated shape that maximizes laminar flow of blood within the aorta. There exists a need for a blood pump which reduces risk of complications associated with excessive arterial blockage.

SUMMARY OF THE INVENTION

The invention provides a blood pump for use with an intravascular ventricular assist system (iVAS), as well as a method for utilizing the blood pump to treat heart failure.

Accordingly, in one aspect, the invention provides a blood pump assembly. The blood pump assembly includes: a) a balloon defining an elongated inflatable chamber, the balloon having a distal end and a proximal end, wherein the distal end is rounded and the proximal end has an opening; and b) an inflation tube coupled to the opening of the proximal end of the balloon, the tube defining a fluid channel in fluid communication with the inflatable chamber. The balloon has a central region having an elongated cylindrical shape when in an inflated state and a substantially planate shape when in an uninflated state thereby promoting laminar flow of fluid within a blood vessel in which the pump is implanted.

In another aspect, the invention provides an intravascular ventricular assist system (iVAS) which includes the blood pump assembly of the disclosure. In embodiments, the iVAS includes a drive unit housing a bellows in fluid communication with the blood pump, an arterial interface device (AID) having a suture ring, a vascular graft and stopper, and a skin interface device (SID).

In yet another aspect, the invention provides a method of providing ventricular assistance to a subject. The method includes implanting the blood pump assembly of the disclosure into a blood vessel of a subject and cycling the blood pump through a series of inflation/deflation cycles.

In still another aspect, the invention provides a method of treating heart failure in a subject. The method includes implanting the blood pump assembly of the disclosure into a blood vessel of a subject and cycling the blood pump through a series of inflation/deflation cycles.

In another aspect, the invention provides a method of introducing a blood pump into a blood vessel of a subject.

BRIEF DESCRIPTION OF THE DRAWINGS

The invention will be better understood from a reading of the following detailed description taken in conjunction with the drawings in which like reference designators are used to designate like elements, and in which:

FIG. 12 schematically shows the inflation tube 21 of FIG. 10;

FIG. 13 is a cross-sectional view of section A-A of the inflation tube depicted in FIG. 12;

FIG. 14 is a cross-sectional view of section B-B of the inflation tube depicted in FIG. 12;

FIG. 15 is an expanded view of detail C of FIG. 12;

FIG. 16 is an expanded view of detail D of FIG. 12;

DETAILED DESCRIPTION OF THE INVENTION

U.S. patent application Ser. Nos. 14/659,375 and 14/476,656, and U.S. Pat. Nos. 8,323,174 and 7,892,162 are incorporated herein in their entireties. The components, devices, modules, source code, and the like, associated with the CAD and components thereof as disclosed in U.S. patent application Ser. Nos. 14/659,375 and 14/476,656, and U.S. Pat. Nos. 8,323,174 and 7,892,162 are also disposed in the CAD and components thereof as described herein. In addition, the functions and methods disclosed in U.S. patent application Ser. Nos. 14/659,375 and 14/476,656, and U.S. Pat. Nos. 8,323,174 and 7,892,162, that utilize those components, devices, modules, source code, and the like, are also operative using the CAD described herein.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

While the blood pump assembly of the present invention is generally disclosed with use of a CAD of the disclosure, it may be utilized with a variety of devices and in a variety of procedures which involve vascular implantation of such devices.

Figure 1:
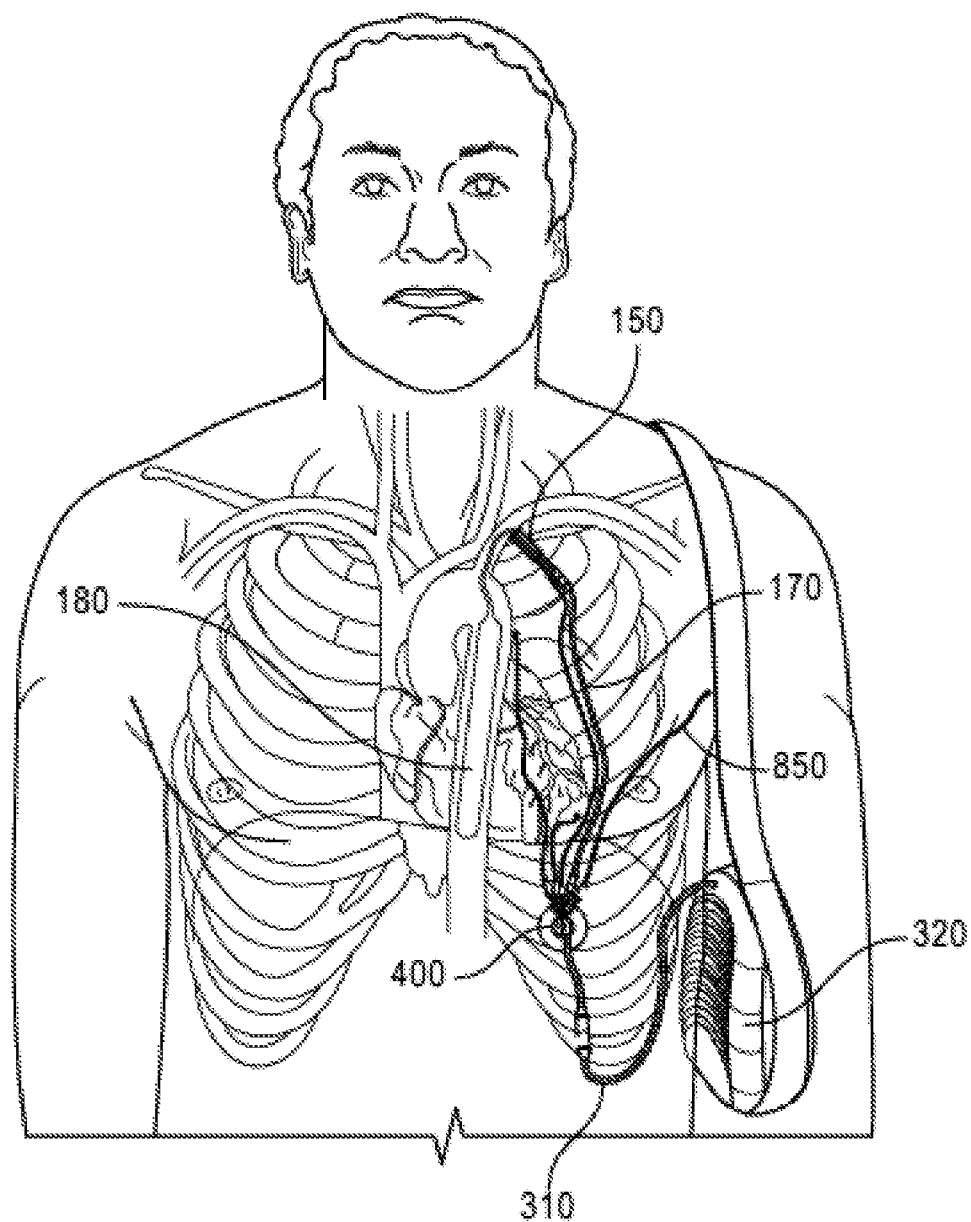
FIG. 1 schematically shows a CAD, also referred to herein as an intravascular Ventricular Assist System (iVAS), including blood pump 180, internal drive line 170, arterial interface device (AID) 150, skin interface device (SID) 400, external drive line 310, external driver 320, and subcutaneous ECG leads 850 superimposed on a human thorax.

In a primary embodiment, the CAD of the disclosure, also referred to herein as an iVAS, operates on the principle of counterpulsation similar to an intra-aortic balloon pump (IABP). Components of the system are shown in FIG. 1. During diastole, pump inflation augments the native heart's cardiac output by displacing blood in the aorta, pushing it downstream. At the start of systole (peak of the R-wave), the pump deflates, decreasing aortic pressure and reducing the work required of the left ventricle during subsequent ejection. Counterpulsation has been a standard treatment for cardiogenic shock for decades, providing circulatory support for hours to weeks.

In various embodiments, implantation of an iVAS requires implanting four components: an arterial interface device (AID), a blood pump, a skin interface device (SID), and internal drive line. To facilitate implantation of the blood pump, custom tools and methodology were developed, including an introducer assembly. Upon implantation, the blood pump undergoes repeated inflation/deflation cycles to assist in driving blood through the arteries. A key factor which is addressed by the present invention is reducing blockage within the artery when the blood pump is in a deflated state during systole. This is accomplished by an innovative blood pump (interchangeably referred to herein as a balloon pump) structure in which the pump is capable of maintaining a substantially flat planar shape when deflated thereby promoting and/or maintaining laminar flow within the blood vessel.

Accordingly, in one aspect, the invention provides a blood pump assembly. With reference to FIGS. 2-5, the assembly 10 includes: a) a balloon 15 defining an elongated inflatable chamber 16, the balloon 15 having a distal end 17 and a proximal end 18, wherein the distal end 17 is rounded and the proximal end 18 has an opening 19; and b) an inflation tube 21 coupled to the opening 19 of the proximal end 18 of the balloon 15, the tube 21 defining a fluid channel in fluid communication with the inflatable chamber 16. The balloon 15 has a central region 25 having an elongated cylindrical shape when in an inflated state and a substantially planate shape when in an uninflated state thereby promoting laminar flow of fluid within a blood vessel in which the pump is implanted.

Figure 2:
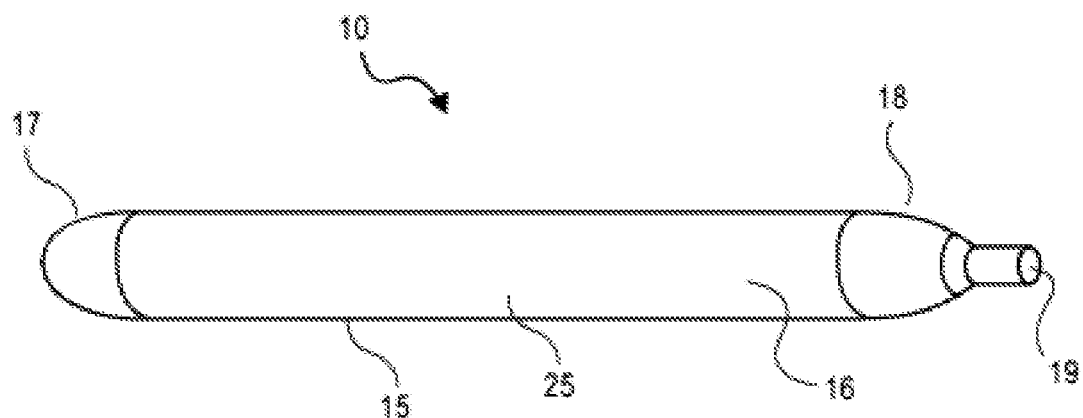
FIG. 2 is a perspective view of a blood pump 10 in one embodiment of the invention.
Figure 3:
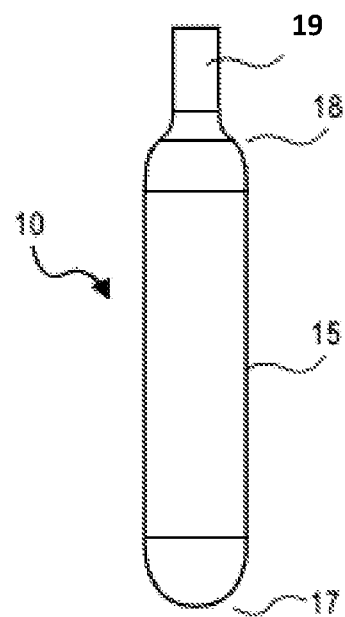
FIG. 3 is a top view of the blood pump depicted in FIG. 2 in a deflated state.
Figure 4:
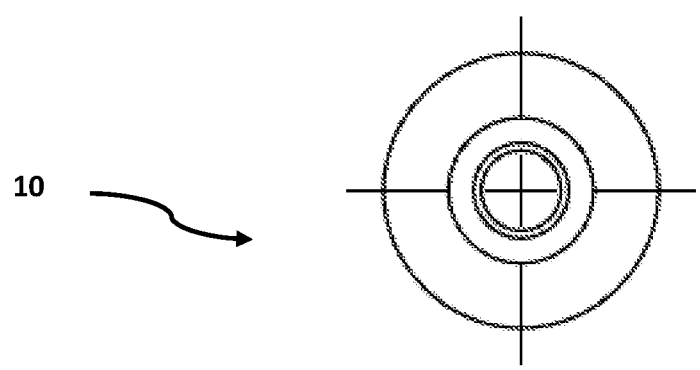
FIG. 4 is a right side view of the blood pump 10 depicted in FIG. 2.
Figure 5:
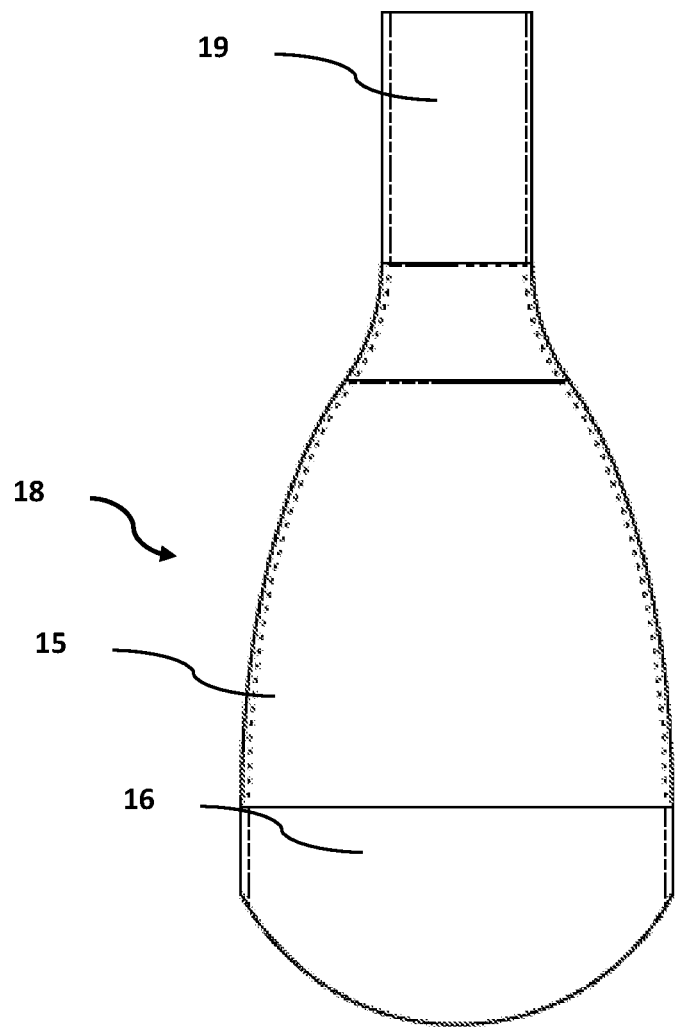
FIG. 5 is an expanded side view of the proximal end of the blood pump depicted in FIG. 2.
Figure 6:
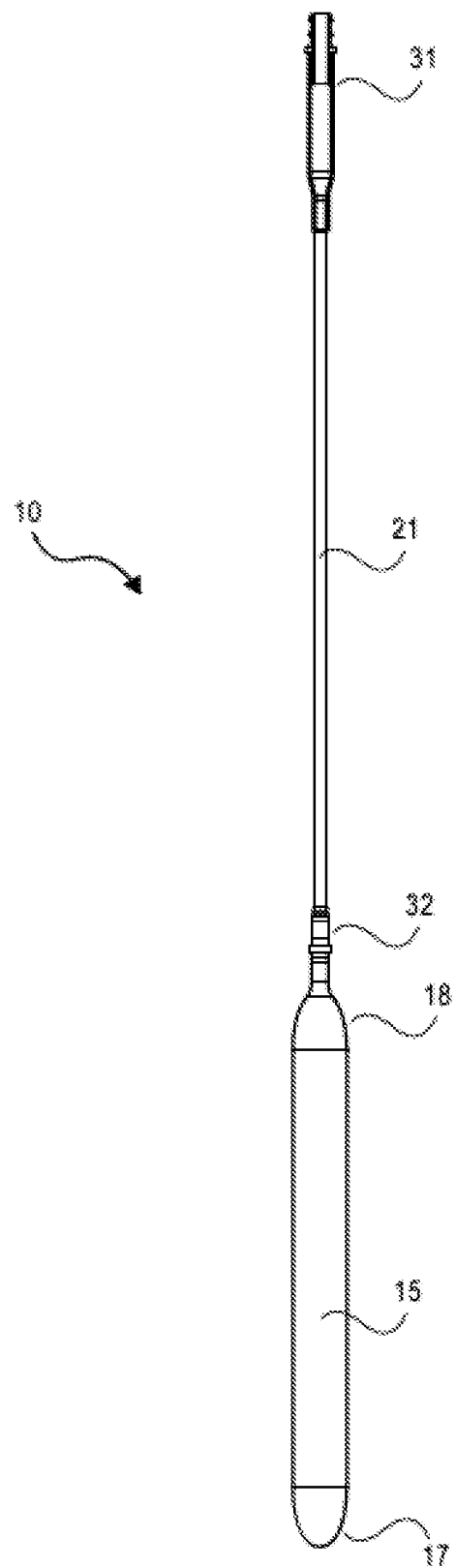
FIG. 6 schematically shows an assembly including blood pump 10 coupled with inflation tube 21.
Figure 7:
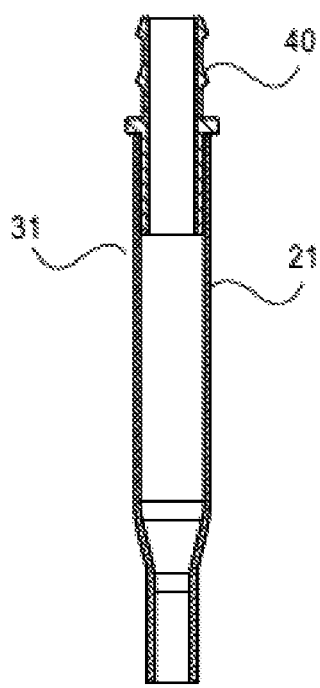
FIG. 7 is a cross-sectional view along the longitudinal axis of the proximal end 31 of the inflation tube 21 depicted in FIG. 6.
Figure 8:
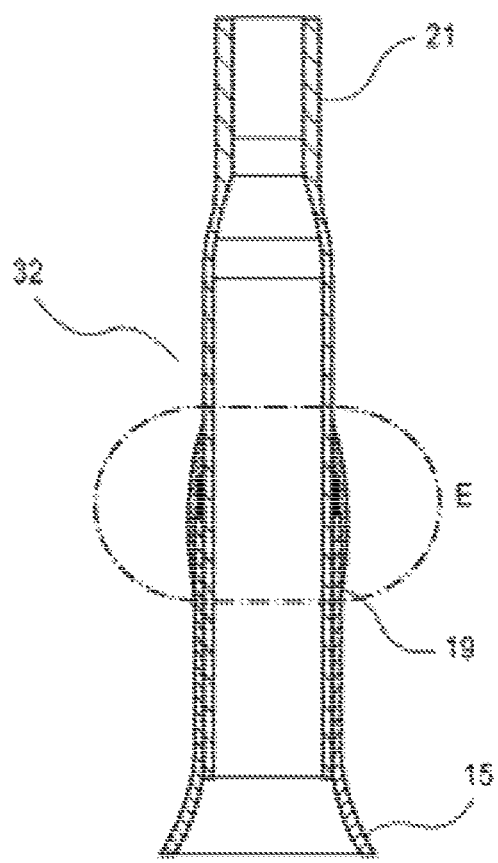
FIG. 8 is a cross-sectional view along the longitudinal axis of the distal end 32 of the inflation tube 21 depicted in FIG. 6 as coupled to the proximal end of the balloon 15 via balloon opening 19.
Figure 22:
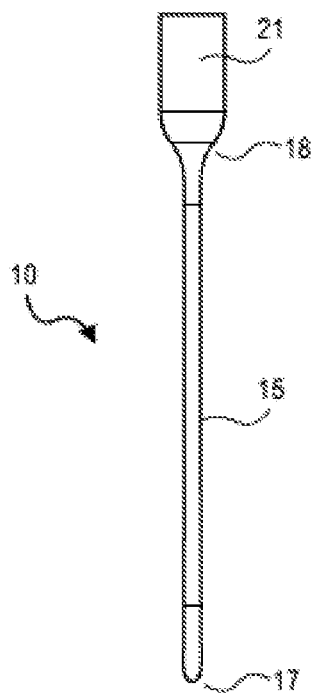
FIG. 22 is a right side view of the pump of FIG. 2 in a deflated state.
Figure 23:
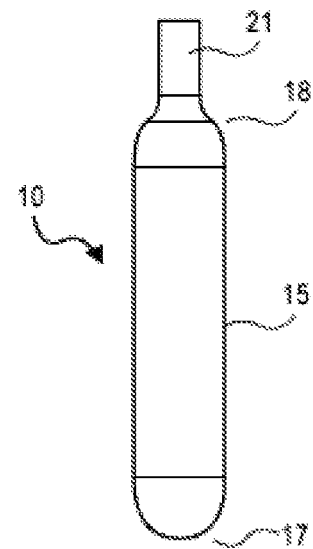
FIG. 23 is a top view of the pump of FIG. 2 in a deflated state.

FIG. 2 illustrates the blood pump 15 when the balloon is in the fully inflated state. Notably, when in a deflated state, the balloon maintains a substantially flat, planate geometry as shown in FIGS. 22-23. FIG. 22 is a side view of the blood pump 10 showing the balloon 15 in a deflated state in which the balloon 15 has a substantially flat, planate structure along the longitudinal axis from the distal end 17 to the proximal end 18 of the balloon 15. The deflated balloon structure is also illustrated in FIG. 23 which is a top view of the balloon having a flattened, and widened profile.

Laminar flow is the normal condition for blood flow throughout most of the circulatory system. It is characterized by concentric layers of blood moving in parallel down the length of a blood vessel. The highest velocity (Vmax) is found in the center of the vessel. The lowest velocity (V=0) is found along the vessel wall. The flow profile is parabolic once laminar flow is fully developed. This occurs in long, straight blood vessels, under steady flow conditions.

The orderly movement of adjacent layers of blood flow through a vessel helps to reduce energy losses in the flowing blood by minimizing viscous interactions between the adjacent layers of blood and the wall of the blood vessel. Disruption of laminar flow leads to turbulence and increased energy losses. During turbulent flow, blood does not flow linearly and smoothly in adjacent layers, but instead the flow can be described as being chaotic. Turbulence increases the energy required to drive blood flow because turbulence increases the loss of energy in the form of friction, which generates heat. As such, increased turbulence requires a higher driving pressure for a given rate of flow which creates unwanted strain on the heart of a subject with chronic heart failure.

The balloon profile in the deflated state promotes uniform laminar flow in the vessel within which it is implanted. As such turbid flow is reduced thereby decreasing the propensity for clotting, creation of stagnant zones and excessive strain on the heart.

Figure 9:
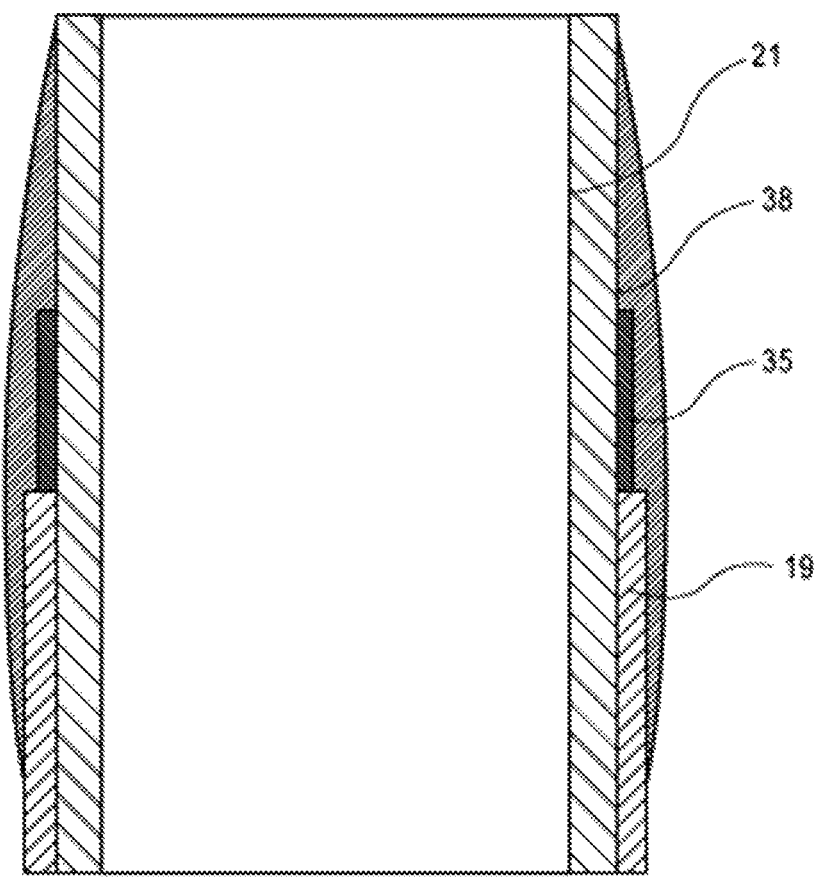
FIG. 9 is an expanded cross-sectional view of detail E of FIG. 8.
Figure 10:
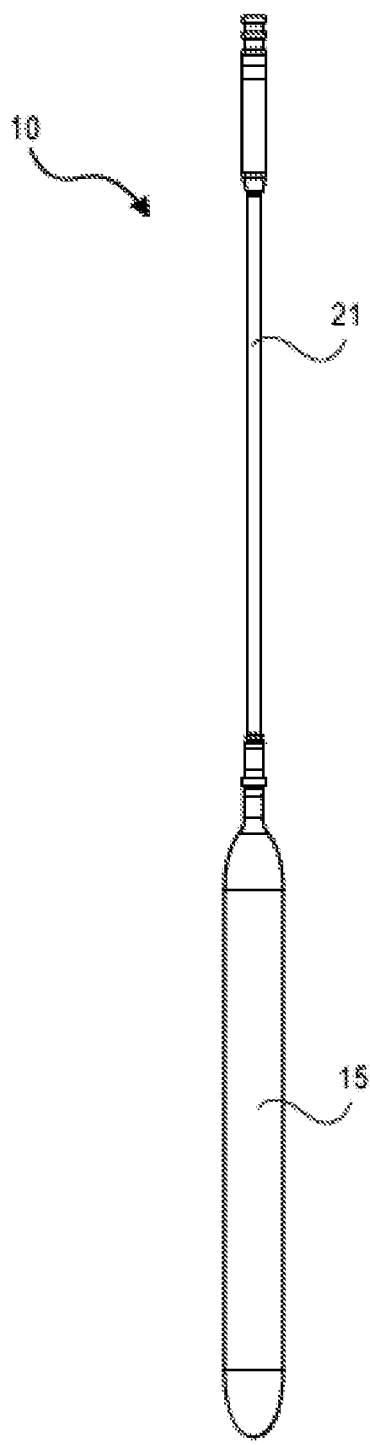
FIG. 10 schematically shows an assembly including balloon 15 coupled with inflation tube 21.
Figure 11:
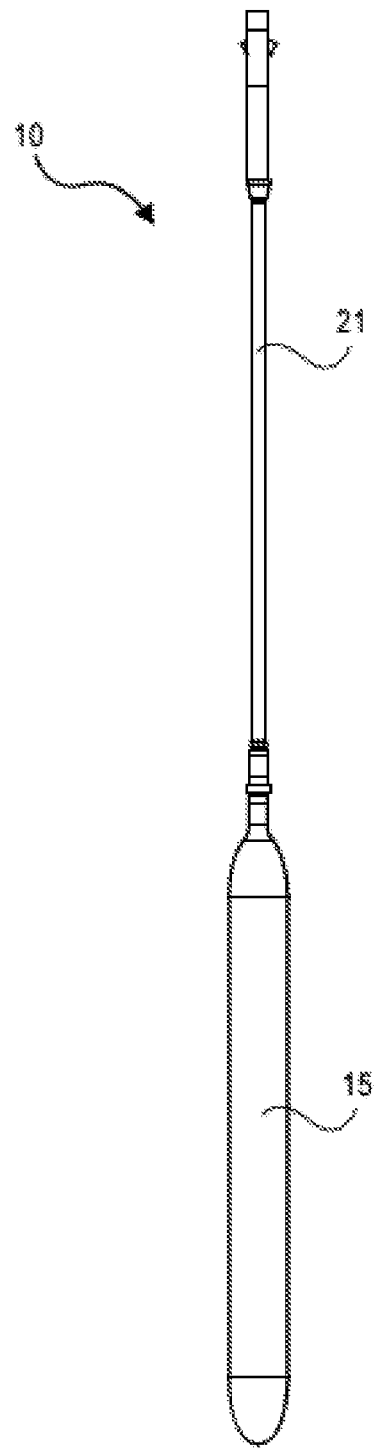
FIG. 11 is a cross-sectional view along the longitudinal axis of the assembly depicted in FIG. 10.
Figure 17:
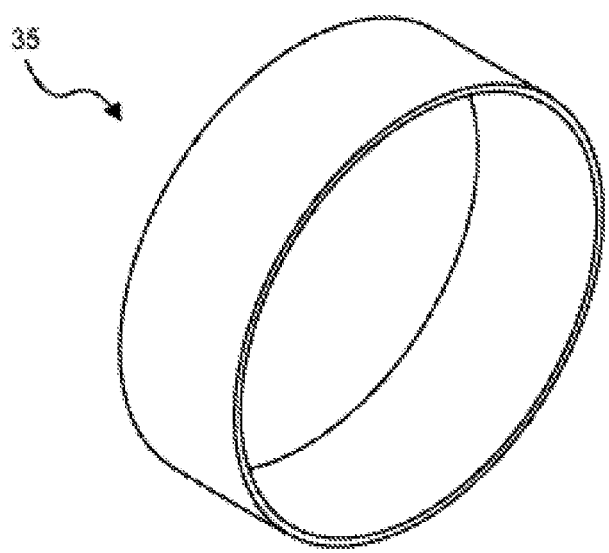
FIG. 17 is a perspective view of the radiopaque marker 35 in one embodiment of the invention.
Figure 18:
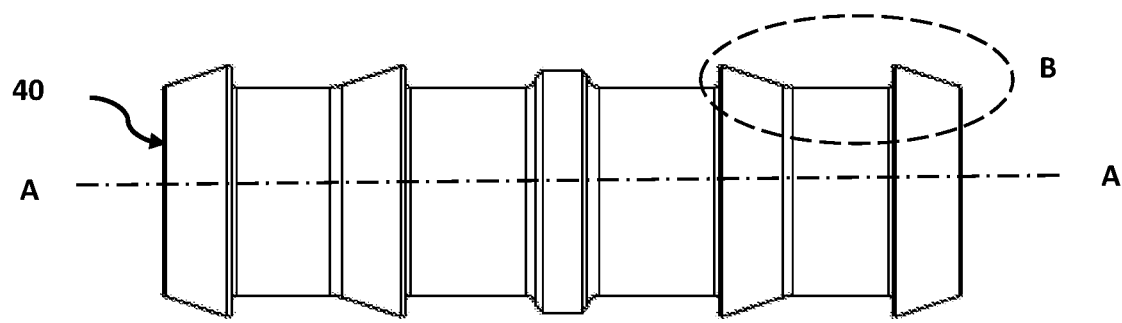
FIG. 18 schematically illustrates the double hose barb 40 for coupling the inflation tube to a drive line in one embodiment of the invention.
Figure 19:
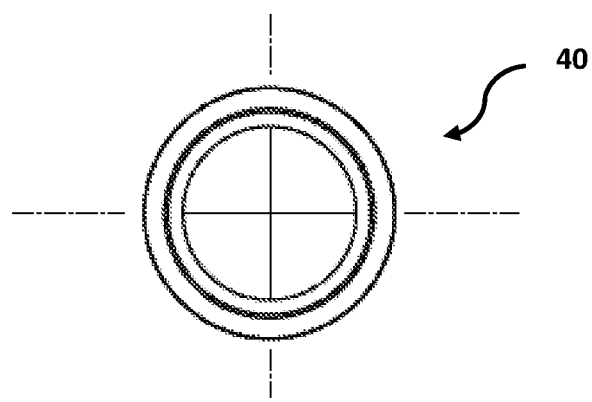
FIG. 19 is a side view of the double hose barb depicted in FIG. 18.
Figure 20:
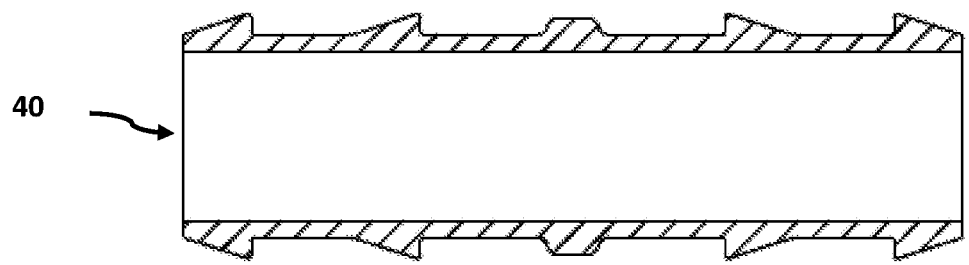
FIG. 20 is a cross-sectional view of section A-A of the double hose barb depicted in FIG. 18.
Figure 21:
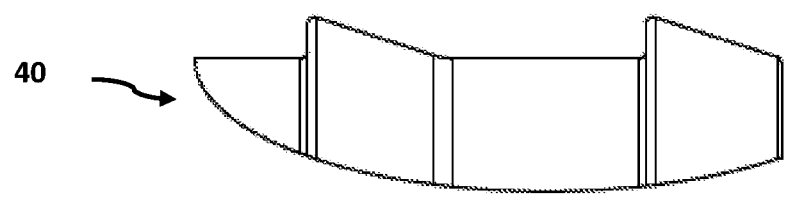
FIG. 21 is an expanded view of detail B of FIG. 18.

The balloon portion 15 of the blood pump assembly 10 is coupled to inflation tube 21. FIGS. 12-16 show several views of inflation tube 21 having proximal end 31 and distal end 32. Distal end 32 of inflation tube 21 couples to opening 19 of balloon 15. The coupled structure is shown in FIG. 9. The distal end 32 of inflation tube 21 is inserted into opening 19 of balloon 15 such that the interior surface of the balloon opening is in contact with the outer surface of inflation tube 21. Optionally, radiopaque ring 35 may be disposed at the coupling site. The surface of the inflation tube 21 and the balloon opening 19 may be solvent bonded together. A coating layer 38 is disposed over the coupling site to further affix balloon 15 to the inflation tube 21. Notably, coating layer 38 also provides a smooth exterior profile to the coupling site so that the exterior surface of the entire assembly has no protrusions that may increase turbid flow upon implantation.

Inflation tube 21 typically has a uniform diameter along its length. In embodiments, the outer diameter of the tube is no greater than 4, 5, 6 or 7 mm. Ideally, the outer diameter is about 7, 6.5, 6, 5.5, 5, 4.5, 4.0 mm or less, such as 6.5, 6.4, 6.3, 6.2, 6.1, 6.0, 5.9, 5.8, 5.7, 5.6, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.2, 3.1, 3.0, 2.9, 2.8, 2.7, 2.6, 2.5 mm or less. In embodiments, the inner diameter of the tube is no greater than 2.5, 3, 3.5, 4, 4.5 or 5 mm. Ideally, the inner diameter is about 5, 4.5, 4.0, 3.5, 3.0 mm or less, such as 5.0, 4.9, 4.8, 4.7, 4.6, 4.5, 4.4, 4.3, 4.2, 4.1, 4.0, 3.9, 3.8, 3.7, 3.6, 3.5, 3.2, 3.1, 3.0, 2.9, 2.8, 2.7, 2.6, 2.5 mm or less. Ideally the inner diameter is about 3.0 to 3.3 mm. In embodiments, the outer diameter is sized such that less than 80, 75, 70, 65, 60, 55, 50, 45% of the cross-sectional area of the blood vessel that it is implanted in is occluded. Ideally the outer diameter is sized such that less than 55, 50 or 45% of the cross-sectional area of the blood vessel that it is implanted in is occluded and the inner diameter is greater than 3.0 mm and the outer diameter is less than 6.0 mm. Ideally the outer diameter is sized such that less than 55, 50 or 45% of the cross-sectional area of the blood vessel that it is implanted in is occluded and the inner diameter is greater than 3.5 mm and the outer diameter is less than 6.0 mm. Ideally the outer diameter is sized such that less than 55, 50 or 45% of the cross-sectional area of the blood vessel that it is implanted in is occluded and the inner diameter is greater than 4.0 mm and the outer diameter is less than 6.0 mm. In embodiments, the inner diameter is about 3.0 to 4.0 mm and the outer diameter is about 4.1 to 6.5 mm. In one embodiment, the inner diameter is about 3.2 mm and the outer diameter is about 4.0. In one embodiment, the inner diameter is about 3.1 mm and the outer diameter is about 4.0. In one embodiment, the inner diameter is about 3.0 mm and the outer diameter is about 4.0. In embodiments, the inner diameter is 3.0, 3.1, 3.2, 3.3, 3.4, 3.5, 3.6, 3.7, 3.8 or 3.9 mm and the outer diameter is 4.0, 4.1, 4.2, 4.3, 4.4, 4.5, 4.6, 4.7, 4.8, 4.9 or 5.0 mm. As will be appreciated by one in the art, the inner diameter must be sized to accommodate the guidewire including any feature which is present at the blunt distal end of the guidewire. As such the blunt distal end will be sized such that the outer diameter of the distal end is less than the inner diameter of the inflation tube.

The wall thickness of inflation tube 21 is typically less than 1 mm, such as 0.9, 0.8, 0.7, 0.6, 0.5 mm or less. To prevent kinking, inflation tube 21 may include a stiffening material, such as a mesh component to add wall stiffness. In one embodiment, the mesh component is a wire mesh, optionally composed of medical grade steel or alloy such as Nitinol®. In such embodiments, the balloon does not require an additional radiopaque marker. Alternative stiffening elements and configurations are known in the art and may be incorporated into the inflation tube wall. For example, polymer fibers, textiles and the like may be utilized. Additionally, the stiffening elements may be incorporated into the inflation tube wall in a variety of geometries, for example, as a mesh, braided or woven textile, helical spiral and the like.

Proximal end 31 of inflation tube 21 is coupled to a pneumatic line, such as an internal drive line which is in fluid communication with a fluid driver having a contractible bellows for inflating and deflating the balloon. As shown in FIGS. 18-21, a double hose barb 40 connects the inflation tube 21 to the pneumatic drive line.

The balloon 15 may be composed of any biocompatible material that provides a smooth exterior profile and is capable of undergoing repeated inflation/deflation cycles. In embodiments, a preferred material includes block copolymers, such as segmented polyether polyurethane. In one embodiment, the balloon is composed essentially of Bio-Span® sold by DSM Biomedical Inc.

The dimensioning of the balloon along with the balloon material are critical in maintaining proper functioning of the device when implanted along with maintaining proper flow parameters as discussed herein. In embodiments, the balloon has a uniform wall thickness along its length which is between about 0.2 to 0.4 mm. In one embodiment, the balloon wall thickness is about 0.3 mm. Further, the length of the balloon is between about 195 to 210 mm, for example, about 200 to 205 mm. In embodiments, the balloon is dimensioned such that it has a volume of between about 40 to 60 cc when inflated. In embodiments, the balloon has an overall deflated thickness of less than about 1.0, 0.9, 0.8, 0.7, 0.6, 0.5 or 0.4 mm. Ideally, the balloon has an overall deflated thickness of between about 0.2-0.8 mm, 0.2-0.4 mm, 0.3-0.6 mm, 0.4-0.6 mm or 0.4-0.8 mm so as to promote laminar flow within the vasculature upon deflation of the balloon.

The balloon must be capable of undergoing a high number of repetitive inflation/deflation cycles without failure upon implantation. Ideally, the balloon has a lifespan of inflation/deflation cycles of greater than about 25, 50, 75, or 100 million cycles. As such the device may remain implanted for the duration of a patient's life upon implantation, for example, 1, 2, 3, 4, 5 years or more.

Figure 24:
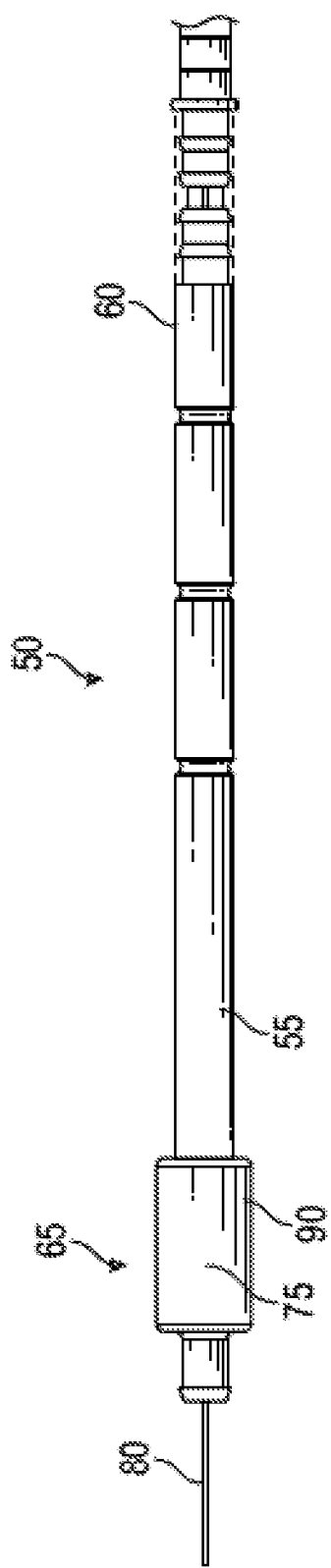
FIG. 24 schematically shows an introducer assembly 50 for use with implanting a blood pump of a CAD in a patient.
Figure 25:
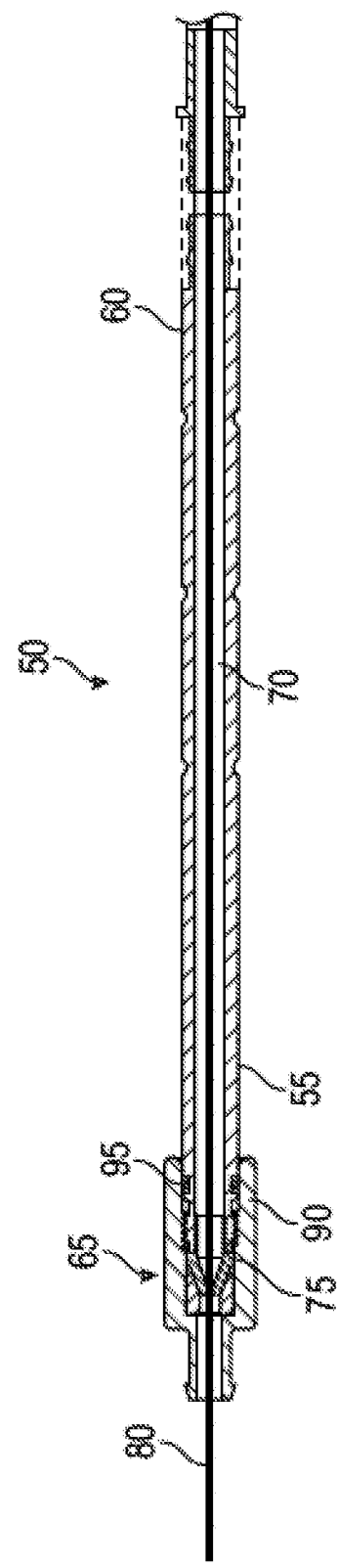
FIG. 25 is a cross-sectional view of the introducer assembly depicted in FIG. 24.
Figure 26:
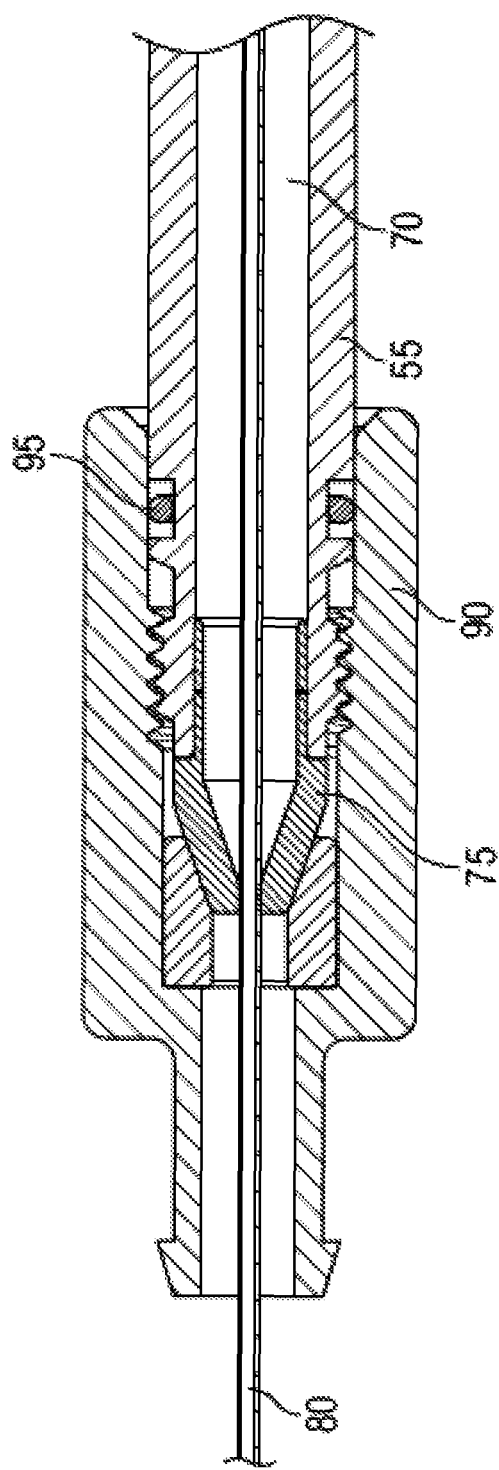
FIG. 26 is an expanded cross-sectional view of locking component 90 and associated collet mechanism 75 of the introducer assembly 50 depicted in FIG. 24.

In one embodiment, the blood pump assembly is implanted using an introducer assembly as shown in FIGS. 24-26. With reference to FIGS. 24-26, the assembly 50 includes: a) a shaft 55 elongated along a longitudinal axis, the shaft having a distal end 60, a proximal end 65, a lumen 70 extending along the longitudinal axis from the distal end 60 to the proximal end 65, and a collet mechanism 75 disposed at the proximal end 65 for receiving a guidewire 80; and b) a locking component 90 having a distal end and a proximal end, the locking component adapted such that the distal end of the locking component reversibly couples to the proximal end of the shaft. The locking component has a locked configuration and an unlocked configuration such that when in the locked configuration, a gripping force is created between the collet mechanism 75 and a guidewire 80 inserted within lumen 70.

Notably, the proximal end 65 of the shaft is adapted to form a fluid tight seal with the locking component 90. This can be accomplished by inclusion of o-ring 95. The fluid tight seal prevents blood loss during introduction of the balloon pump 180 into the vasculature. The o-ring 95 also creates an air tight seal between the introducer and the pump 180 allowing the pump to be deflated during insertion into the vasculature.

Figure 28A:
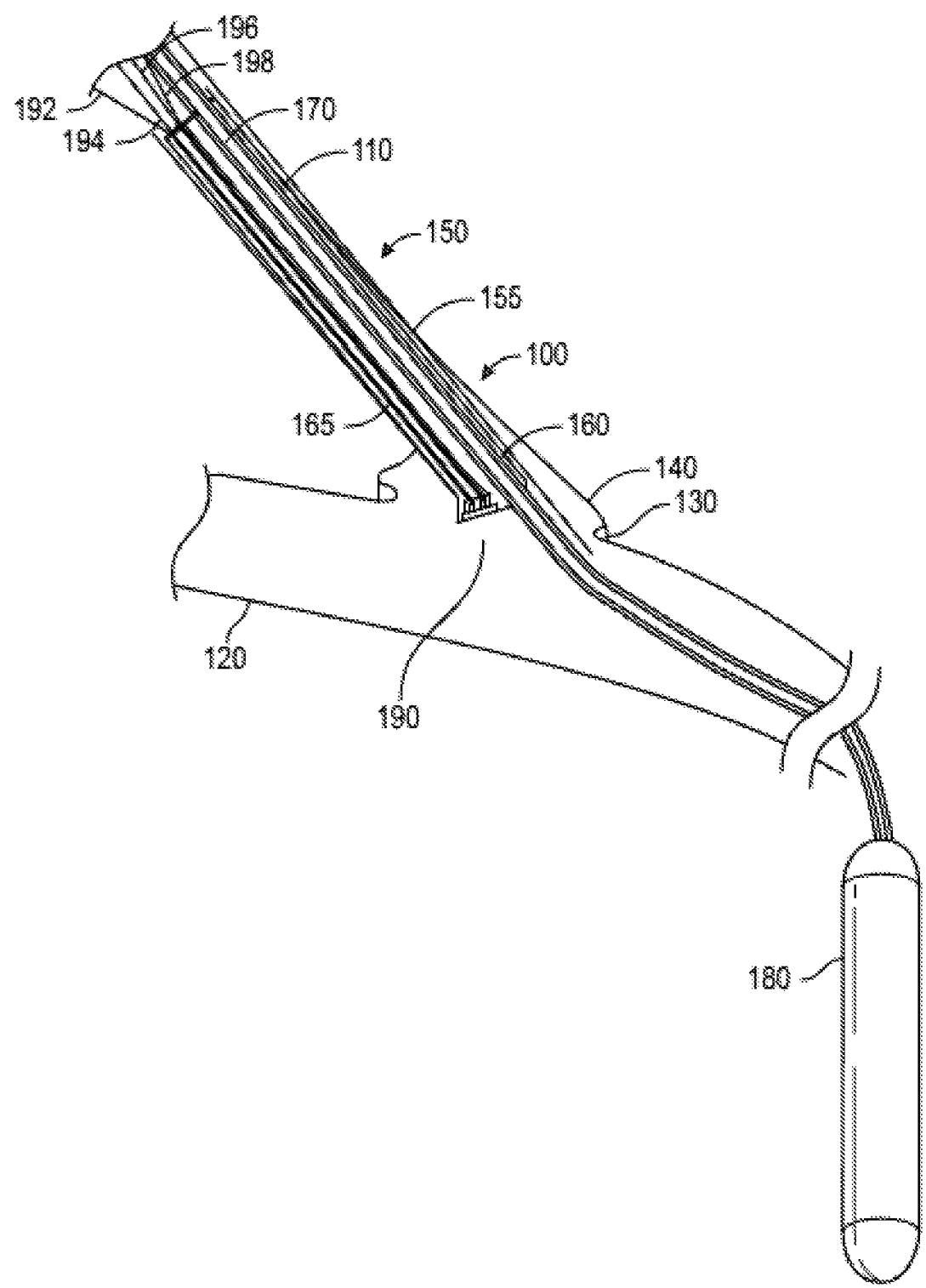
FIG. 28A schematically shows a CAD implanted in a patient using an AID 150.
Figure 28B:
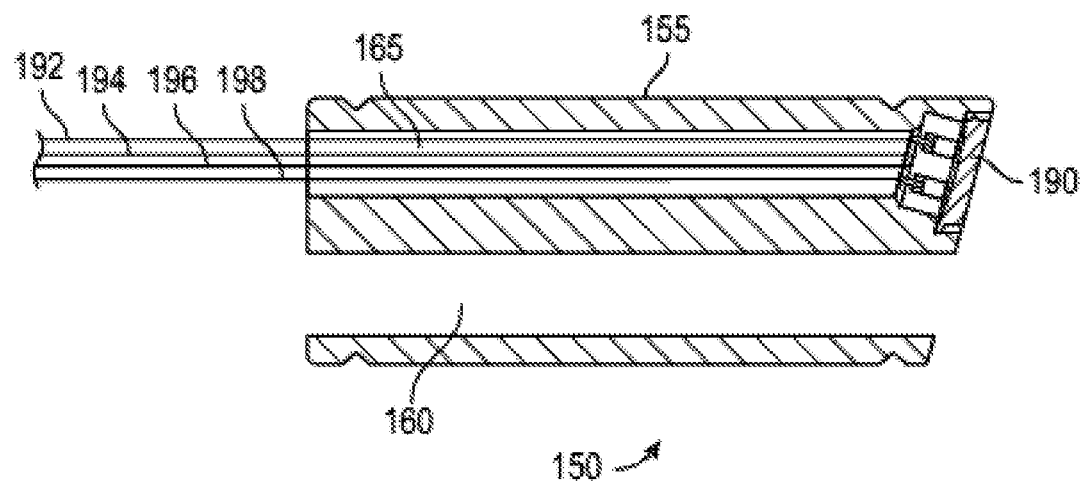
FIG. 28B is a cross-sectional view of AID 150.

FIGS. 28A and 28B illustrate an AID 150 of the iVAS. Referring to FIG. 28A, a vascular interface 100 is formed using a vascular AID graft 110 attached to an artery 120 with a suture ring 130 at the position of an incision in the artery. The particular graft shown flares at its distal end 140. AID 150 sits inside the AID graft 110, filling the interior of the AID graft 110.

Sewing the suture ring 130 to the subclavian artery is the first task the surgeon performs when implanting the system. Next, AID graft 110 is sutured to the suture ring 130.

With reference to FIGS. 28A and 28B, AID 150 comprises a body 155. In certain embodiments, body 155 comprises a polyurethane. In certain embodiments, body 155 comprises a polysiloxane. In the illustrated embodiment of FIGS. 28A and 28B, body 155 is formed to include two lumens extending therethrough. Lumen 160 is utilized to pass pneumatic drive line 170 through AID 150.

Figure 29A:
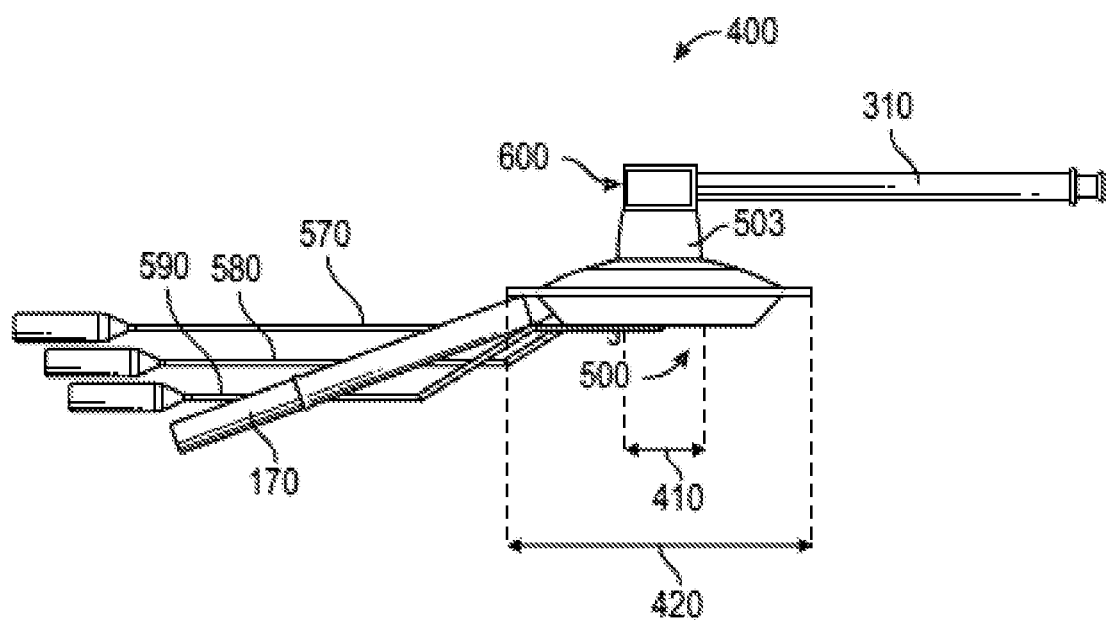
FIG. 29A illustrates a skin interface device (SID) 400 comprising an implantable base 500 and a SID cap 600.
Figure 29B:
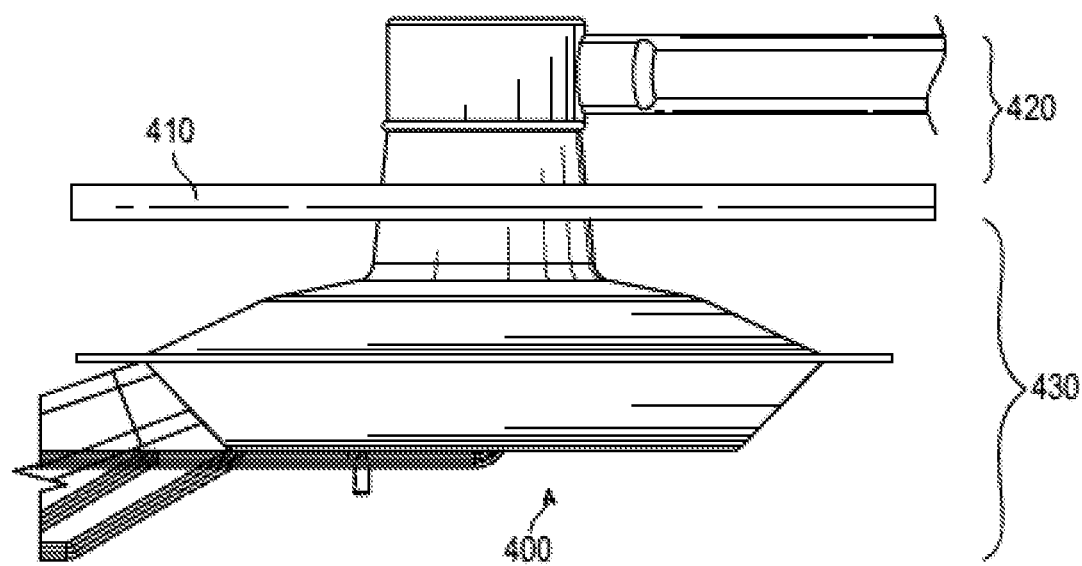
FIG. 29B illustrates a supracutaneous portion 420 and a subcutaneous portion 430 of the SID 400 when disposed within a patient.

The second lumen 165 optionally houses a pressure sensor 190 to measure arterial pressure, and sensor leads 192, 194, 196, and 198, to interconnect sensor 190 to SID 400 (FIGS. 29A and 29B). Sensor leads 192, 194, 196, and 198, are used to provide power to sensor 190, provide a ground connection, to provide clock signals to sensor 190, and to communication arterial pressure signals from sensor 190 to SID 400.

Lumen 160 which extends through the length of the AID 150 is filled by the pneumatic drive line 170. Pneumatic drive line 170 in turn is connected at its distal end to a pump 180. In certain embodiments, inflation catheter is formed to have an inner diameter in the range 3 to 6 mm (often about 5 mm), although other diameters are possible as well.

Not shown in FIG. 28A is the proximal end of the pneumatic drive line 170. Because the pump 180 needs to inflate and deflate in coordination with the cardiac cycle in order to function as a ventricular assist device, the pump must be in fluid communication with a driver (for example, an air compressor or pump) via the pneumatic drive line 170.

In embodiments wherein such a driver is external to the body as shown in FIG. 1, the SID 400 (FIGS. 29A and 29B) allows the design of the system to be composed of parts both implanted and external to the patient's body. The pneumatic drive line 170 is attached to SID 400, and SID 400 is attached to the fluid driver. In certain embodiments, the driver, the pneumatic drive line 170 and the pump 180 form a closed air system, wherein that closed system includes a well-defined and precisely controlled volume of air. Such a well-defined and precisely-controlled volume of air facilitates leak detection.

In certain embodiments, air volume and movement of air is precisely controlled using, for example and without limitation, a bellows driven by one or more linear actuators. In descriptions of the skin interface device herein, the pneumatic drive line 170 is alternatively referred to as an internal drive line.

In implantation of the balloon pump 180, once the anastomosis of the suture ring 130 and AID graft 110 is complete as discussed above, an access port containing an iris valve (FIG. 30) is inserted into the graft's proximal end creating hemostasis. The surgeon then attaches a sheath (FIG. 31) to the proximal end of the port. Inside the sheath is the blood pump 180 in its deflated state. The other end of the sheath is tied off to the shaft of the introducer assembly as illustrated in FIG. 31. The function of the access port is to minimize blood loss during pump insertion. The sheath is used to collect any blood that escapes through the access port.

Figure 30:
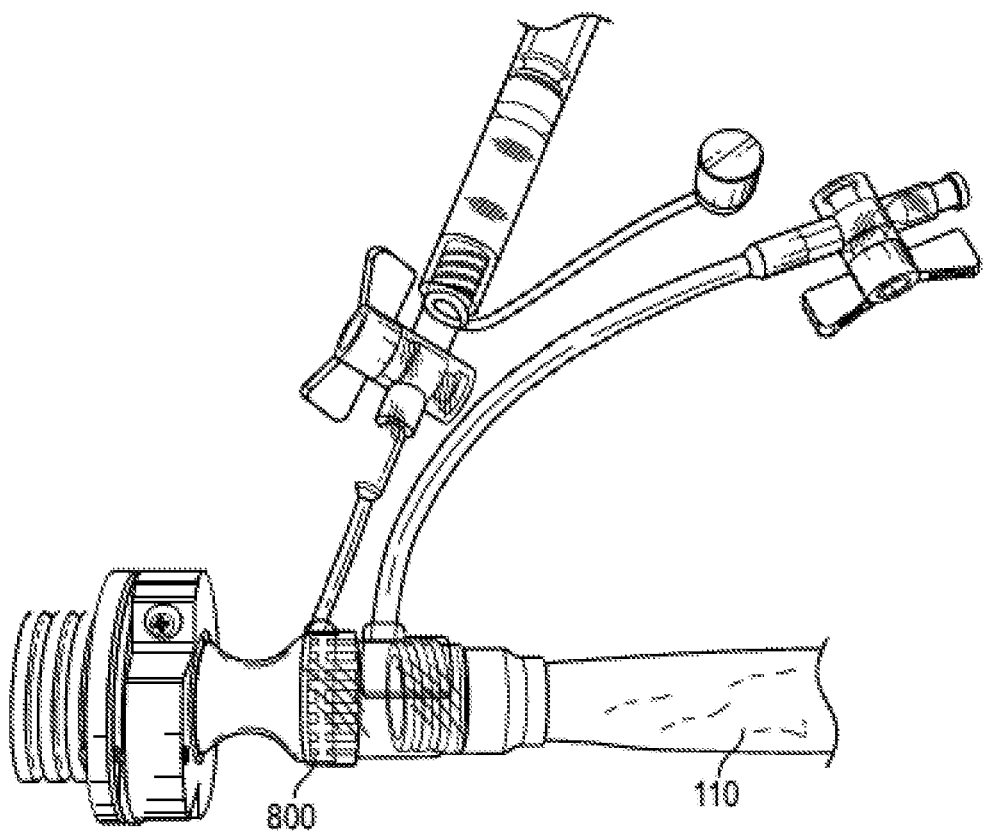
FIG. 30 shows an access port assembly 800 used to occlude an AID graft 110 during implantation of a balloon pump.
Figure 31:
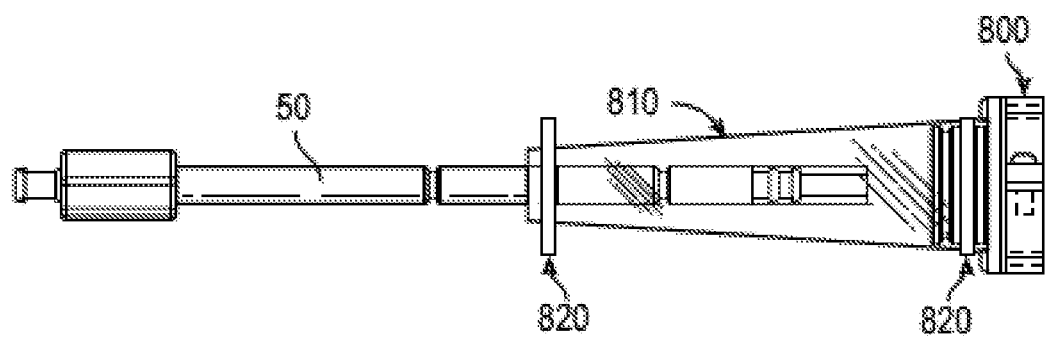
FIG. 31 shows an assembly of introducer assembly 50 in combination with an access port 800 and sheath 810 during implantation of a balloon pump.

With reference to FIGS. 30 and 31, in implantation of the blood pump 180, once the anastomosis of the suture ring 130 and AID graft 110 is complete as discussed above, an access port assembly 800 optionally containing an iris valve (FIG. 30) is inserted into AID graft 110 at its proximal end creating hemostasis. The surgeon then optionally attaches a sheath 810 (FIG. 31) to the proximal end of the access port assembly 800. Inside the sheath 810 is the blood pump 180 in its deflated state. The other end of the sheath 810 is tied off to the shaft of the introducer assembly 50 as illustrated in FIG. 31. The sheath 810 is attached to the access port assembly 800 and shaft of the introducer assembly 50 via sutures 820. The function of the access port is to minimize blood loss during pump insertion. The sheath is used to collect any blood that escapes through the access port. The blood pump 180 is then implanted in the patient's vasculature, i.e., the descending thoracic aorta. To implant the pump, the surgeon inserts and guides it down the patient's subclavian artery, traverses the subclavian aorta bifurcation, and then travels down the aorta to the final location. The pump does not have the mechanical rigidity to permit implantation without the introducer 50.

In embodiments, the sheath is not required in implantation. In such embodiments, in implantation of the blood pump 180, once the anastomosis of the suture ring 130 and AID graft 110 is complete as discussed above, an access port assembly 800 containing an iris valve (FIG. 30) is inserted into AID graft 110 at its proximal end creating hemostasis. The sheath is not required since AID graft 110 may be reversibly clamped to prevent blood loss. The blood pump 180 is then implanted in the patient's vasculature, i.e., the descending thoracic aorta. To implant the pump, the surgeon inserts and guides it down the patient's subclavian artery, traverses the subclavian aorta bifurcation, and then travels down the aorta to the final location. The pump does not have the mechanical rigidity to permit implantation without the introducer 50.

Figure 27:
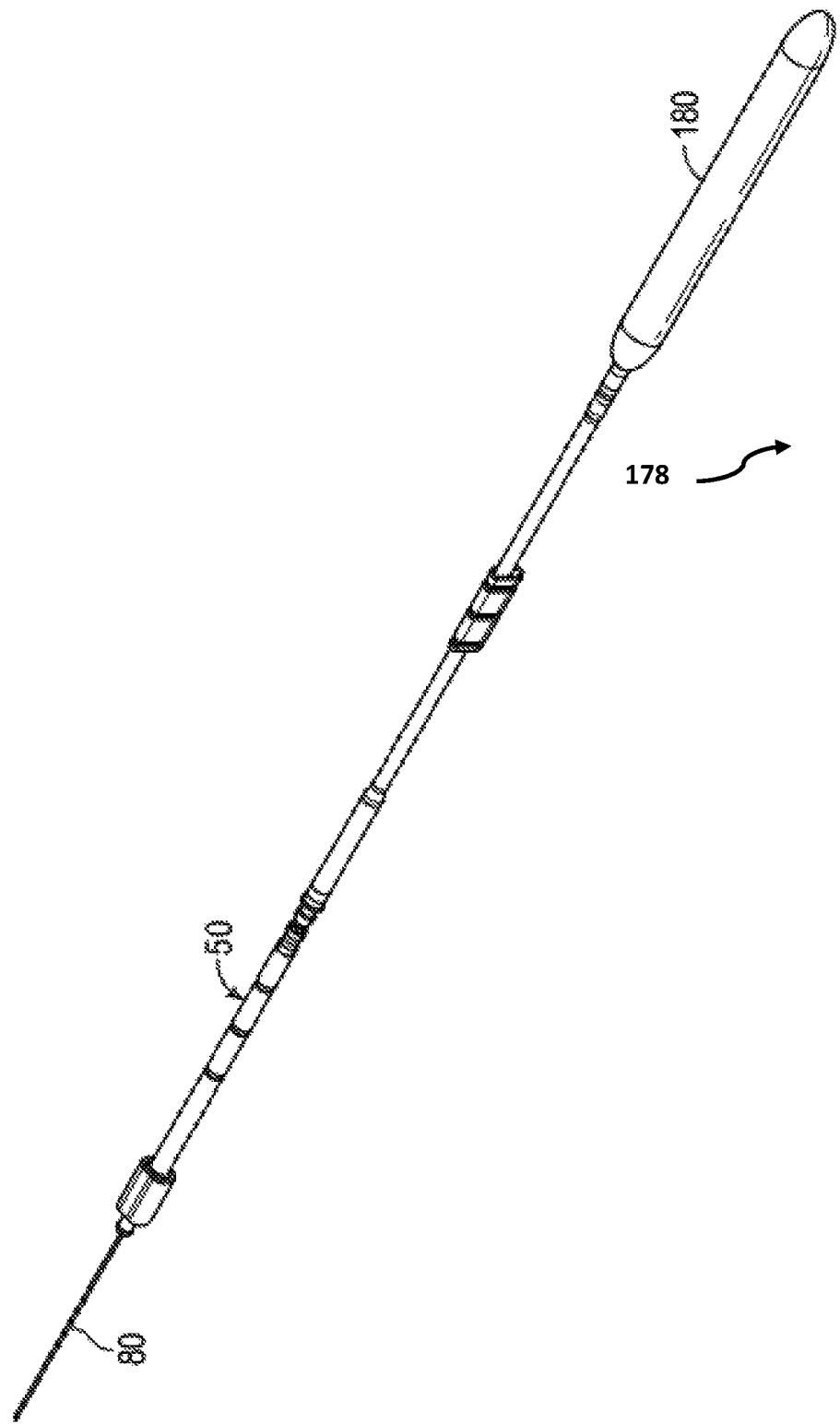
FIG. 27 schematically shows the introducer assembly 50 coupled to balloon pump 180 during implantation of the pump.
Figure 32:
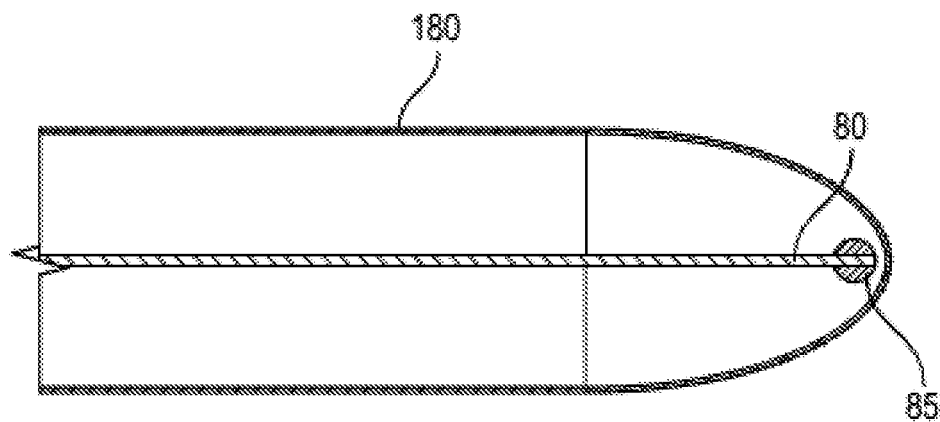
FIG. 32 is an expanded cross-sectional view of a distal portion of a balloon pump 180 in which a blunt distal end 85 of guidewire 80 is advanced to the distal tip of the balloon during delivery.
Figure 33:
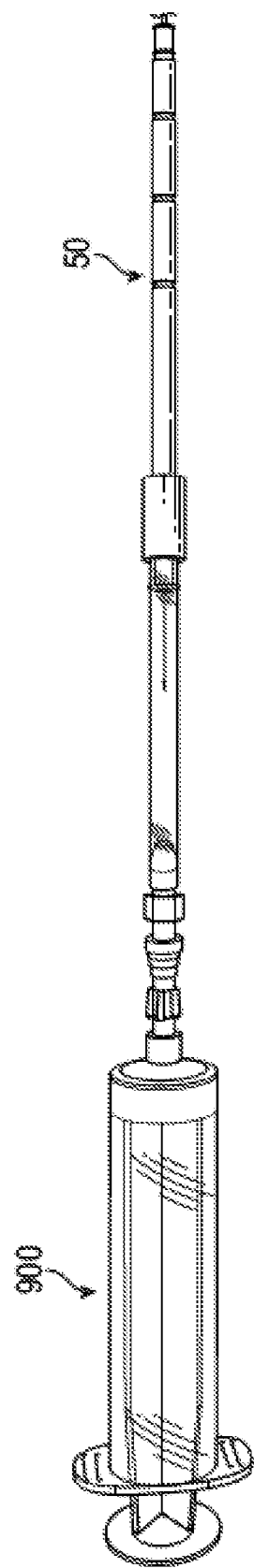
FIG. 33 shows an assembly of introducer assembly 50 in combination with a vacuum source (syringe) during implantation of a balloon pump.

In one embodiment, during installation of the balloon pump 180, guidewire 80 is inserted into the balloon pump so the wire's blunt distal end 85 contacts the distal inside tip of the pump (FIG. 32). Thus the guidewire 80 is within the central lumen of the balloon pump 180 during insertion as opposed to being in an auxiliary lumen or on the outside surface of the balloon. This allows the balloon to have a single lumen, the balloon being of uniform thickness along its length. The distal end of the introducer shaft is then mechanically attached to the proximal end of the pump as shown in FIG. 27. Collet mechanism 75 and associated locking component 90 are used to lock the guidewire 80 into place. A vacuum device (i.e., a syringe as in FIG. 33) is then used to pull a vacuum on the pump (not shown) minimizing its size. Once the pump is placed, the vacuum is released, the guidewire 80 is extracted and the shaft is removed.

In embodiments, the access port assembly 800 may be removed during implantation of the blood pump 180. As such, the inner diameter of the port may be sized large enough such that it can accommodate the AID 150 and the introducer assembly 50. For example, once the blood pump 180 is placed within the artery, the access port assembly 800 may be detached and slid away from the patient over the introducer assembly 50 and guidewire 80. In embodiments, the inner diameter of the access port is greater than about 3, 4, 5, 6, 7, 8, 9, 10, 11, 12, 13, 14 or 15 mm. In one embodiment, the inner diameter of the access port is equal to or greater than about 7 or 8 mm.

To facilitate placement and detection of the balloon pump 180 during installation, the guidewire 80, or portion thereof, may include a radiopaque material. For example, blunt end 85 may be composed of or otherwise include a radiopaque material. Alternatively, the balloon pump 180, or portion thereof, may include a radiopaque material. In one embodiment, the balloon includes a ring of radiopaque material adjacent and proximal to the inflation region of the balloon. For example, the balloon pump 180 may include a ring composed of Pt—Ir alloy. In another embodiment, both the guidewire 80, or portion thereof, and the balloon pump 180, or portion thereof include a radiopaque material.

Figure 34:
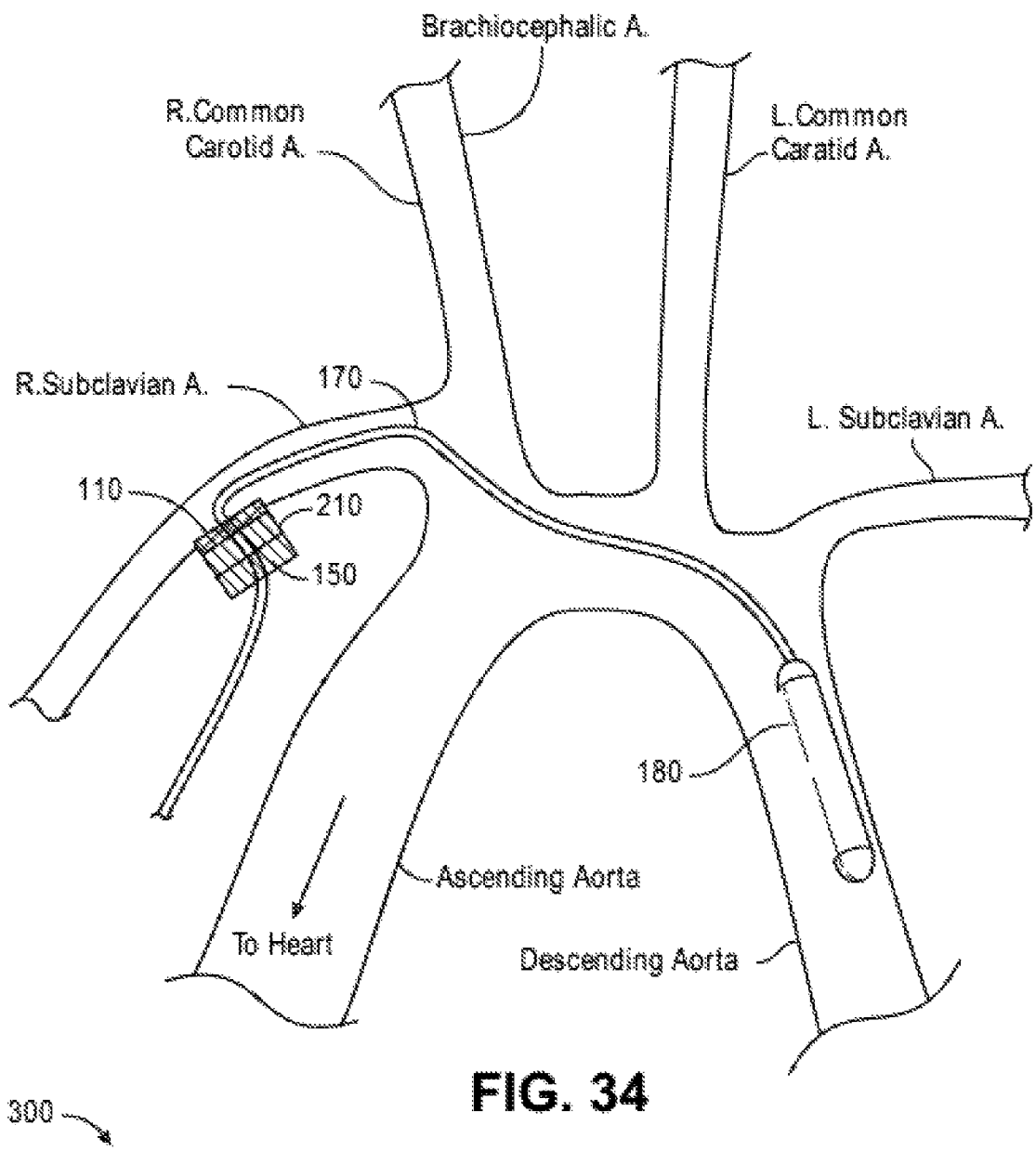
FIG. 34 schematically shows a pump positioned in the proximal descending aorta, with the pump's inflation catheter entering the vasculature at the right subclavian artery through AID 150.

FIG. 34 shows (schematically) the AID graft 110 in position on the right subclavian artery. This position is advantageous because it allows easy surgical access and a relatively short distance to the descending aorta. FIG. 34 also shows the graft secured to AID 150 by a suture 210. Other suitable positions for the interface include either common carotid artery, the brachiocephalic artery, the left subclavian artery, the descending aorta, and the abdominal aorta. Downstream branches of the aorta may also be used, such as the external iliac and femoral arteries.

In embodiments, implantation of the balloon pump 180 may be achieved without the assistance of an introducer assembly. For example, the balloon pump 180 may be positioned within the vasculature by pulling the pump into and through the vasculature. Once blunt distal end 85 of the guidewire 80 is advanced to the distal inside tip of the pump, a snare device is used to grasp the blunt distal end 85 and pull the balloon pump 180 into position within the vasculature. The procedure is described as follows.

Figure 36:
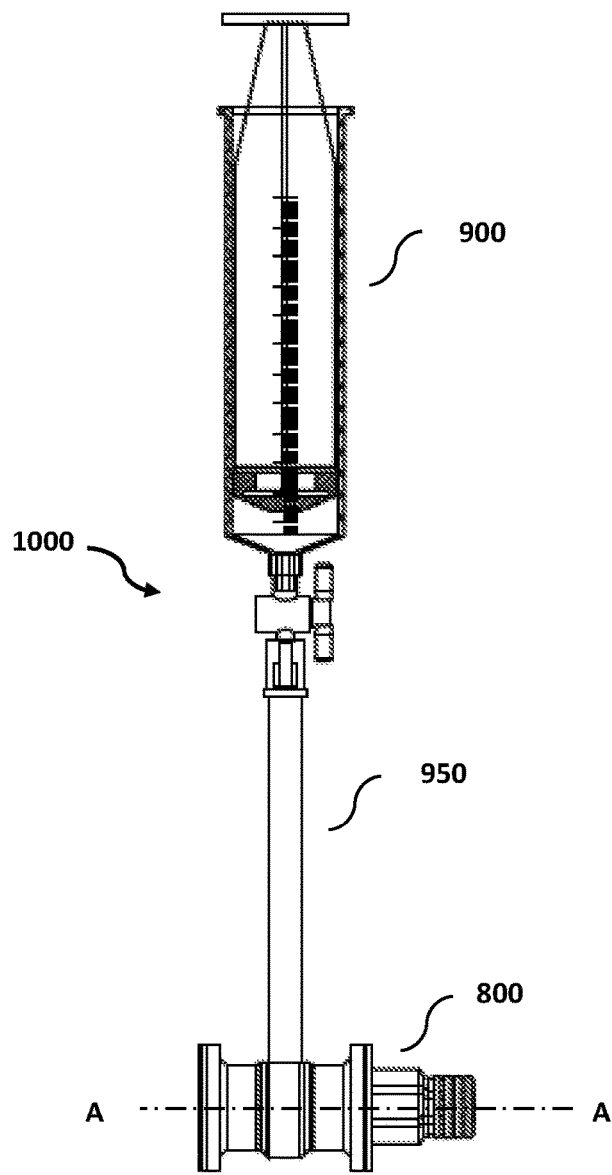
FIG. 36 shows an access port assembly 1000 used to occlude an AID graft during implantation of a balloon pump.
Figure 37:
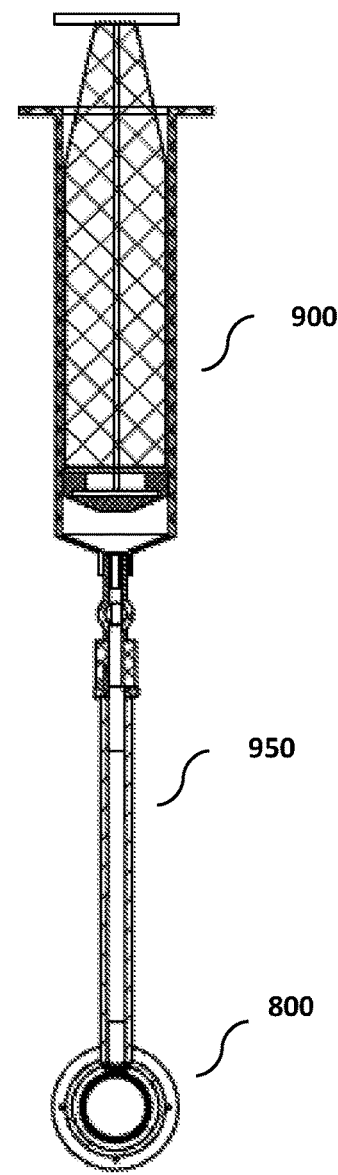
FIG. 37 is a cross-sectional view of the access port assembly of FIG. 36 along the longitudinal axis.
Figure 38:
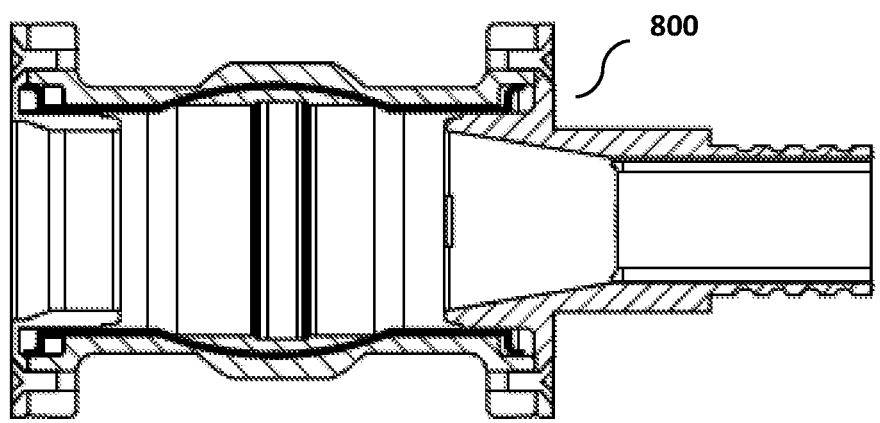
FIG. 38 is a cross-sectional view of section A-A of the access port assembly of FIG. 36.

As discussed above, sewing the suture ring 130 to the subclavian artery is performed and AID graft 110 is sutured to the suture ring 130. Once the anastomosis of the suture ring 130 and AID graft 110 is complete, an access port is inserted into the graft's proximal end and the port is occluded. FIGS. 36-38 illustrate an access port in one embodiment invention. As shown in FIGS. 36-38, access port 800 is shown coupled to syringe 900 via tubing 950.

The surgeon next advances the guidewire 80 into the vasculature to visualize future pump placement in the aorta and determine the appropriate length of pump to implant (for example, pump having overall length including integral drive line of 12 inches or 16 inches). The guidewire 80 is then removed from the vasculature.

The snare device is then introduced into the femoral artery and advanced along the vasculature until the distal tip of the snare device exits the vasculature via the access port. The snare device generally includes an elongated flexible shaft having a distal tip configured to reversibly grasp or couple with the blunt distal end 85 of the guidewire 80. Further, the elongated flexible shaft of the snare device is of sufficient length such that the proximal end of the shaft remains outside of the vasculature at the femoral artery insertion point when the distal tip of the shaft is advanced through the access port 800 to exit the vasculature. To facilitate advancement of the snare device to the access port at the subclavian artery, the snare device may be coupled to a wire, for example a J-wire, which is placed in the vasculature above stream of the snare device and used to pull the snare device to the access port. In embodiments, guidewire 80 is used to pull the snare device to the access port.

The blunt distal end 85 of the guidewire 80 and the distal tip of the snare device may be configured in any number of geometries that allow for reversible attachment to one another without damaging the tip of the balloon. In one embodiment, the blunt distal end 85 has a smooth rounded geometry, such as a sphere or ellipsoid to prevent the guidewire from piercing the distal end of the balloon while also providing a structure for the grasping structure of the distal tip of the snare device to couple with. One in the art would understand that the grasping structure of the snare device may be configured in a variety of ways to facilitate coupling with the blunt distal end 85 of the guidewire while avoiding damage to the balloon. For example, the grasping portion may be configured as a wire snare, grasping jaws, slotted member for receiving the blunt distal end, and the like. In some embodiments, the distal end of the guidewire may include a groove, notch or recess to engage the grasping mechanism. In some embodiments, the distal end of the guidewire may include a bump or protrusion to engage the grasping mechanism.

Figure 40:
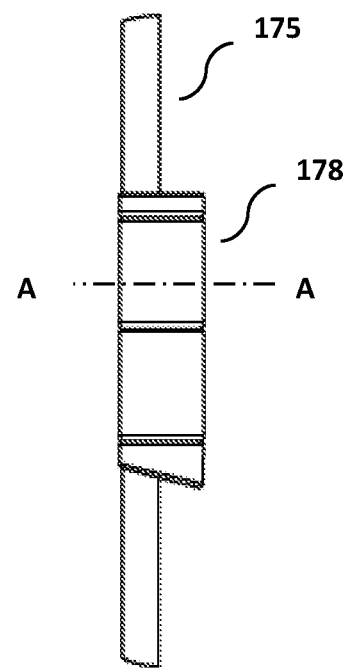
FIG. 40 is an expanded view of detail A of FIG. 39.

Next, the surgeon inserts the guidewire 80 into the balloon pump 180 and advances blunt distal end 85 to the distal tip of the balloon pump while the balloon pump 180 remains outside of the patient. The distal end of the snare device is coupled with the blunt distal end 85, for example via a wire loop, and the balloon pump 180 is introduced into the vasculature through the access port 800 (i.e., access port 800 as in FIGS. 36-37) by progressively withdrawing the shaft of the snare device from its femoral artery point of entry thereby pulling the balloon along the vasculature into position within the descending aorta. The access port 800 is optionally simultaneously actuated to permit blood pump insertion while minimizing blood loss. Before the balloon pump 180 is introduced into the vasculature, a vacuum device is optionally used to pull a vacuum on the pump minimizing its size. This can be accomplished via the use of a Tuohy Borst valve coupled at the proximal end 179 of the drive line 175 as shown in FIG. 40 along with a vacuum device coupled to the valve. Upon placement of the balloon pump as discussed below, the vacuum is released and the guidewire 80 is extracted. In alternative embodiments, FIG. 36 illustrates an access port 800 coupled to syringe 900 via tubing 950 which may be used to pull a vacuum on balloon pump 180.

To visualize insertion and correct placement of the balloon pump 180 within the vasculature, fluoroscopy, or any other suitable imaging method known in the art is used. In one embodiment, the blunt distal end 85 of the guidewire 80 along with radiopaque marker 35 located distally on the balloon pump 180 are used as visual markers to ensure correct placement.

Figure 39:
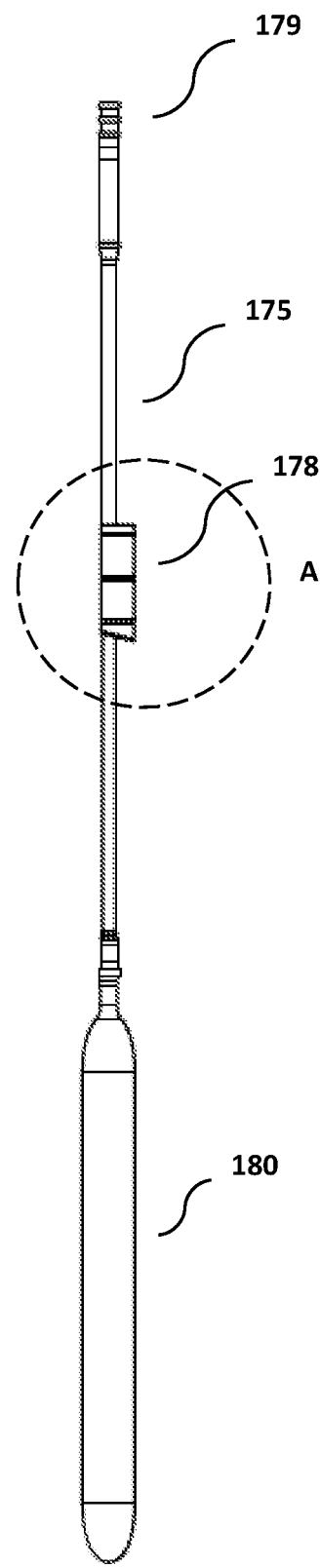
FIG. 39 schematically shows an assembly having a balloon pump 180 fluidly coupled to drive line 175 which has AID stopper 178 disposed on the drive line.
Figure 41:
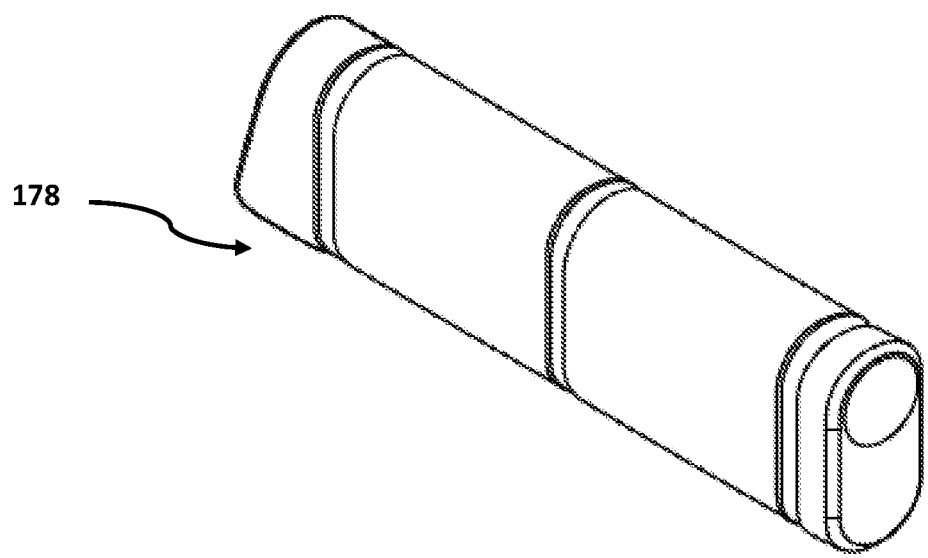
FIG. 41 is a perspective view of the AID stopper 178 of FIG. 40.
Figure 42:
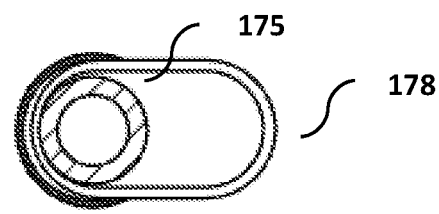
FIG. 42 is a cross-sectional view of section A-A of detail A of FIG. 40.
Figure 43:
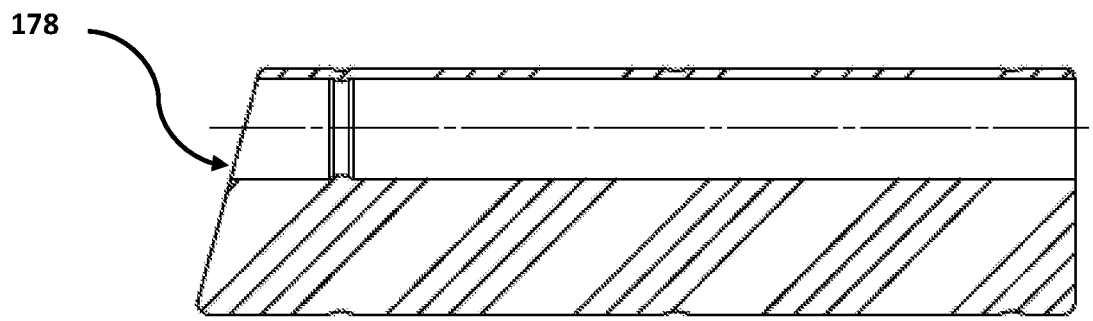
FIG. 43 is a cross-sectional view of the AID stopper 178 of FIG. 41.

Once the balloon pump 180 is at the desired position, a stopper portion of the AID is inserted into the graft portion of the AID. FIG. 39 shows an assembly including balloon pump 180 connected to drive line 175 which has AID stopper 178. The drive line 175 extends through the central lumen of the AID stopper 178. FIGS. 41 and 43 illustrate an AID stopper 178 in an embodiment of the invention.

Sutures are then tied around the AID graft 110, AID stopper 178 and drive line 175 to secure the balloon pump's location within the vasculature. The surgeon then uncouples the distal end of the snare device from the blunt distal end 85 of the guidewire 80 at the distal end of the pump. The snare is then withdrawn from the vasculature and the guidewire 80 is also withdrawn from the balloon pump 180.

To ensure that the lumen of the drive line 175 is not overly compressed by suture tension, a gauge device may be used to measure or monitor the inner diameter of the drive line 175 in the region of the drive line 175 that traverses through the lumen of the AID stopper 178. In one embodiment, the gauge device is a malleable rod having a predetermined outer diameter which is advanced into the lumen of the drive line to monitor the inner diameter of the drive line. The sutures may be adjusted if the surgeon determines that the drive line is compressed. This ensures that gaseous fluid flow into the balloon is not restricted which would inhibit optimal performance of the system.

In one embodiment, positioning of the pump within the vasculature is secured without the use of sutures. In this embodiment, a clamp is utilized which is placed over the AID graft 110, AID stopper 178 and drive line 175. The clamp is presized to engage the AID graft 110 and AID stopper 178 without overly compressing the drive line 175. In embodiments, the clamp may be an elongated clamp, optionally hinged, which is configured to encircle the AID graft 110, AID stopper 178 and drive line 175.

Figure 35:
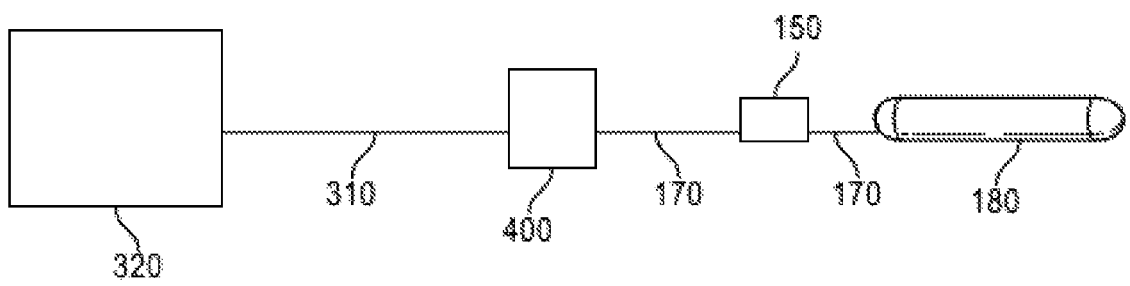
FIG. 35 schematically shows a cardiac assist device 300 including an intra-aortic pump 180, an internal drive line 170, an arterial interface device 150, a skin interface device 400, an external drive line 310, and an external driver 320.

Referring now to FIG. 35, in embodiments, a CAD or WAS comprises a pump 180, a pneumatic drive line 170, an AID 150, a SID 400, an external drive line 310, and an external driver 320.

At its proximal end, the pump 180 is connected to the distal end of the pneumatic drive line 170. An AID 150 is sized and shaped to pass the pneumatic drive line 170 through an arterial wall.

SID 400 connects the proximal end of the pneumatic drive line 170 to the distal end of the external drive line 310. The proximal end of the external drive line 310 is connected to the driver 320.

The pump 180, the internal drive line 170, the SID 400, the external drive line 170, and the driver 320 can be charged with a pumping medium. In certain embodiments, the pumping medium comprises a fluid. A preferred pumping medium is air. In certain embodiments, pump 180, the pneumatic drive line 170, the SID 400, the external drive line 310, and the driver 320 define a closed fluid system. In certain embodiments, pump 180, the pneumatic drive line 170, the SID 400, the external drive line 310, and the driver 320 comprise an open system, wherein the bolus of air inside the system can be exchanged with the ambient environment.

As those skilled in the art will appreciate, pump 180 may have various sizes depending on the anatomy of the patient. In certain embodiments, pump 180 will typically have an inflated volume of about 40 to 60 cubic centimeters when inflated to 10 to 20 mmHg above the maximum systolic pressure.

Internal drive line 170 typically has a uniform diameter along its length. In embodiments, the outer diameter of the drive line is no greater than 4, 5, 6 or 7 mm. Ideally, the outer diameter is about 7, 6.5, 6, 5.5, 5, 4.5, 4.0 mm or less, such as 6.5, 6.4, 6.3, 6.2, 6.1, 6.0, 5.9, 5.8, 5.7, 5.6, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.2, 3.1, 3.0, 2.9, 2.8, 2.7, 2.6, 2.5 mm or less. In embodiments, the inner diameter of the tube is no greater than 2.5, 3, 3.5, 4, 4.5 or 5 mm. Ideally, the inner diameter is about 5, 4.5, 4.0, 3.5, 3.0 mm or less, such as 5.0, 4.9, 4.8, 4.7, 4.6, 4.5, 4.4, 4.3, 4.2, 4.1, 4.0, 3.9, 3.8, 3.7, 3.6, 3.5, 3.2, 3.1, 3.0, 2.9, 2.8, 2.7, 2.6, 2.5 mm or less. Ideally the inner diameter is about 3.0 to 3.3 mm. In embodiments, the outer diameter is sized such that less than 80, 75, 70, 65, 60, 55, 50, 45% of the cross-sectional area of the blood vessel that it is implanted in is occluded. Ideally the outer diameter is sized such that less than 55, 50 or 45% of the cross-sectional area of the blood vessel that it is implanted in is occluded and the inner diameter is greater than 3.0 mm and the outer diameter is less than 6.0 mm. Ideally the outer diameter is sized such that less than 55, 50 or 45% of the cross-sectional area of the blood vessel that it is implanted in is occluded and the inner diameter is greater than 3.5 mm and the outer diameter is less than 6.0 mm. Ideally the outer diameter is sized such that less than 55, 50 or 45% of the cross-sectional area of the blood vessel that it is implanted in is occluded and the inner diameter is greater than 4.0 mm and the outer diameter is less than 6.0 mm. In embodiments, the inner diameter is about 3.0 to 4.0 mm and the outer diameter is about 4.1 to 6.5 mm. In one embodiment, the inner diameter is about 3.2 mm and the outer diameter is about 4.0. In one embodiment, the inner diameter is about 3.1 mm and the outer diameter is about 4.0. In one embodiment, the inner diameter is about 3.0 mm and the outer diameter is about 4.0. In embodiments, the inner diameter is 3.0, 3.1, 3.2, 3.3, 3.4, 3.5, 3.6, 3.7, 3.8 or 3.9 mm and the outer diameter is 4.0, 4.1, 4.2, 4.3, 4.4, 4.5, 4.6, 4.7, 4.8, 4.9 or 5.0 mm. As will be appreciated by one in the art, the inner diameter must be sized to accommodate the guidewire including any feature which is present at the blunt distal end of the guidewire. As such the blunt distal end will be sized such that the outer diameter of the distal end is less than the inner diameter of the inflation tube.

The wall thickness of internal drive line 170 is typically less than 1 mm, such as 0.9, 0.8, 0.7, 0.6, 0.5 mm or less. To prevent kinking, the drive line may include a stiffening material, such as a mesh component to add wall stiffness. In one embodiment, the mesh component is a wire mesh, optionally composed of medical grade steel or alloy such as Nitinol®. In such embodiments, the balloon does not require an additional radiopaque marker. Alternative stiffening elements and configurations are known in the art and may be incorporated into the drive line wall. For example, polymer fibers, textiles and the like may be utilized. Additionally, the stiffening elements may be incorporated into the drive line wall in a variety of geometries, for example, as a mesh, braided or woven textile, helical spiral and the like.

In certain embodiments, sensors are connected to one or more communication interfaces that, like the pneumatic drive line 170, pass through the AID 150 and AID graft 110 and connect to SID 400. In certain embodiments, these one or more communication interfaces provide data to a controller.

In certain embodiments, one or more sensors transmit data, by wire or wirelessly, to Applicants' SID 400. Examples of sensors include, without limitation, electrical leads to measure an electrocardiogram, sensors to detect body temperature, sensors to detect blood analytes (such as blood gases), sensors to detect intra-arterial pressure directly or indirectly, and/or sensors to measure humidity within pump 180. Indirect sensors include, for example and without limitation, a microphone to monitor heart sounds.

In certain embodiments, a controller 530 is disposed in SID 400. In certain embodiments, a controller 530 is integral with external driver 320.

In certain embodiments, signals from one or more sensors are used by controller 530 to monitor the cardiac cycle and, thereby, the counterpulsation cycle. In certain embodiments, combinations of signals from one or more sensors are used by controller 530 to monitor the cardiac cycle.

In certain embodiments, sensors are used to determine the state of the air inside the system. In certain embodiments, air pressure is measured to determine whether the pump is properly inflating, or if there is a leak in the system. In certain embodiments, data from the air pressure sensor is communicated to controller 530.

In certain embodiments, sensors for arterial blood pressure at the pump 180 and/or at the AID 150 are in communication with controller 530. In certain embodiments, these sensors communicate a detected arterial blood pressure to the controller 530, either by wire or wirelessly.

Referring now to FIG. 29A, SID 400 comprises a SID base 500 and a SID cap 600. SID base 500 and SID cap 600 are coupled so as to create an air-tight conduit between the pneumatic drive line 170 and external air line 310. In this way, pneumatic drive line 170, SID 400, and external air line 310, can be part of a closed fluid system. In certain embodiments, an air-tight seal is formed using gaskets and other sealing systems.

Referring now to FIGS. 29A and 29B, when implanted skin interface device 400 includes a SID base 500, comprising a subcutaneous portion 430 internal to the patient, in combination a supracutaneous portion 420. SID cap 600 is attached to the supracutaneous portion 420 of SID base 500. Those skilled in the art will appreciate that it is possible to implant SID 400 in a variety of different locations on the patient, for example abdominally or thoracically.

Referring now to FIG. 29A, SID 400 wirelessly provides electrical energy from SID cap 600 to SID base 500, and also wirelessly and bi-directionally passes electrical signals, i.e. data, between SID cap 600 and SID base 500. In order to optimize the transmission of power from SID cap 600 to SID base 500, and at the same time optimize the transmission of data between SID cap 600 and SID base 500, Applicants have "decoupled" the transmission of power from the transmission of data. The transmission of power from SID cap 600 to SID base 500 is done by induction.

Although the invention has been described with reference to the above examples, it will be understood that modifications and variations are encompassed within the spirit and scope of the invention. Accordingly, the invention is limited only by the following claims.

What is claimed is:

1. A blood pump assembly comprising:
   a balloon defining an elongated inflatable chamber, the balloon having an inflatable distal end and a proximal end, wherein the distal end is rounded and the proximal end has a cylindrical region including an opening; and
   an inflation tube coupled to the opening of the proximal end of the balloon via a coating layer disposed over a coupling site to affix the balloon to the inflation tube, the coating layer providing a smooth exterior profile to the coupling site so that an exterior surface of the assembly is configured to couple the balloon to the inflation tube and provide a smooth transition from the balloon to the inflation tube, and the inflation tube defining a fluid channel in fluid communication with the inflatable chamber;
   wherein, between the inflatable distal end and the proximal end, the balloon has a central region having an elongated cylindrical shape when in an inflated state, and wherein a distalmost end of the inflation tube is coupled to the cylindrical region of the proximal end of the balloon such that the balloon has a substantially flat planar shape when in an uninflated state, the substantially flat planar shape and the coating layer being configured to promote laminar flow of fluid within a blood vessel in which the balloon is implanted when the balloon is in the uninflated state.

2. The blood pump assembly of claim 1, wherein the balloon is composed of a biocompatible material.

3. The blood pump assembly of claim 2, wherein the balloon is composed of a block copolymer.

4. The blood pump assembly of claim 3, wherein the balloon is composed of a segmented polyether polyurethane.

5. The blood pump assembly of claim 1, wherein the balloon is configured such that the distal end of the balloon deflates before the proximal end of the balloon upon transitioning from the inflated state to the uninflated state.

6. The blood pump assembly of claim 1, wherein the distal end of the balloon has a thickness less than that of the proximal end of the balloon.

7. The blood pump assembly of claim 1, wherein the balloon has a uniform thickness along its entire length.

8. The blood pump assembly of claim 7, wherein the balloon has a deflated thickness between 0.2 to 0.8 mm.

9. The blood pump assembly of claim 8, wherein the deflated thickness is between 0.25 to 0.35 mm.

10. The blood pump assembly of claim 1, further comprising a radiopaque marker adjacent the opening of the proximal end of the balloon.

11. The blood pump assembly of claim 10, wherein the radiopaque marker is composed of Pt—Ir alloy.

12. The blood pump assembly of claim 10, wherein the marker is a ring disposed over an exterior surface of the inflation tube.

13. The blood pump assembly of claim 1, wherein the opening is disposed over an exterior surface of the inflation tube, and wherein an interior surface of the opening is bonded to the exterior surface of the inflation tube.

14. The blood pump assembly of claim 13, further comprising an outer layer of biocompatible material disposed over the opening of the balloon, wherein the outer layer is configured to couple the balloon to the inflation tube and provide the smooth transition from the balloon to the inflation tube.

15. The blood pump assembly of claim 14, wherein the outer layer is composed of a block copolymer.

16. The blood pump assembly of claim 15, wherein the outer layer is composed of a segmented polyether polyurethane.

17. The blood pump assembly of claim 1, wherein the elongated cylindrical shape has a first diameter at the distal end of the balloon and a second diameter at the proximal end of the balloon, and wherein the first diameter is less than the second diameter.

18. The blood pump assembly of claim 1, wherein the elongated cylindrical shape has a constant diameter (D1) along its length.

19. The blood pump assembly of claim 18, wherein the opening is circular and has a diameter of D2 which is smaller than D1.

20. The blood pump assembly of claim 19, wherein the balloon smoothly tapers from D1 to D2.

21. The blood pump assembly of claim 19, wherein D1 is between 17 to 22 mm.

22. The blood pump assembly of claim 19, wherein D2 is between 3.0 to 7.5 mm.

23. The blood pump assembly of claim 19, wherein D1 is between 18 to 20 mm and D2 is between 4 to 7 mm.

24. The blood pump assembly of claim 1, wherein the entire external surface of the assembly is smooth.

25. The blood pump assembly of claim 1, wherein the elongated cylindrical shape has, a length of between 195 to 210 mm.

26. The blood pump assembly of claim 25, wherein the elongated cylindrical shape has a length of between 200 to 205 mm.

27. The blood pump assembly of claim 1, wherein the balloon has a volume of between 40 to 60 cc when inflated or 50 cc when inflated.

28. The blood pump assembly of claim 1, wherein the balloon has a rated burst pressure of greater than 10 psi.

29. The blood pump assembly of claim 1, wherein the balloon has a lifespan of inflation/deflation cycles of greater than 25, 50, 75, or 100 million cycles.

30. The blood pump assembly of claim 1, wherein the cylindrical region of the proximal end of the balloon includes an interior surface in contact with an exterior surface of the distalmost end of the inflation tube.

31. The blood pump assembly of claim 1, wherein the inflation tube includes a helical stiffening element incorporated in a wall of the inflation tube.

32. An intravascular ventricular assist system (iVAS), comprising the blood pump assembly of claim 1.

33. The iVAS of claim 32, further comprising a drive unit housing a bellows in fluid communication with the elongated inflatable chamber.

34. The iVAS of claim 32, further comprising an arterial interface device (AID) comprising a suture ring, a vascular graft and stopper.

35. The iVAS of claim 32, further comprising a skin interface device (SID).

36. The iVAS of claim 35, wherein the SID comprises:
a SID cap rotatably coupled to a SID base, both the cap and base being configured to couple to pneumatic drive lines; and
an air-tight conduit between the cap and base for transmitting air through the SID; wherein the base is fluidly coupled to the elongated inflatable chamber of the balloon via a first pneumatic drive line and the cap is fluidly coupled to the bellows via a second pneumatic drive line.

37. A method of treating heart failure in a subject comprising implanting the blood pump assembly of the iVAS of claim 32 into a blood vessel of a subject and cycling the blood pump through a series of inflation/deflation cycles.

38. A method of providing ventricular assistance to a subject via counterpulsation comprising implanting the blood pump assembly of the iVAS of claim 32 into a blood vessel of a subject and cycling the blood pump through a series of inflation/deflation cycles.

39. The method of claim 38, wherein the subject has heart failure.

40. The method of claim 38, wherein the blood pump remains implanted for greater than 1, 2, 3, 4 or 5 years.

41. A method of providing ventricular assistance to a subject via counterpulsation comprising implanting the blood pump assembly of claim 1 into a blood vessel of a subject and cycling the blood pump through a series of inflation/deflation cycles.

42. The method of claim 41, wherein the subject has heart failure.

43. The method of claim 41, wherein the blood pump remains implanted for greater than 1, 2, 3, 4 or 5 years.

44. A method of treating heart failure in a subject comprising implanting the blood pump assembly of claim 1 into a blood vessel of a subject and cycling the blood pump through a series of inflation/deflation cycles.

45. A method of introducing a blood pump into a blood vessel of a subject, the method comprising: providing an access to the subclavian artery; providing an access to the femoral artery; advancing a snare device along the femoral artery from the femoral artery access to the subclavian artery access; advancing a guidewire into the inflatable chamber of the blood pump assembly of claim 1; coupling a blunt distal end of the guidewire at the distal end of the balloon with the snare device; withdrawing the snare device from the femoral artery access thereby pulling the balloon into the descending aorta; uncoupling the snare device from the blunt distal end of the guidewire; withdrawing the snare device from the vasculature; and withdrawing the guidewire from the balloon and subsequently the vasculature.

46. The method of claim 45, further comprising securing the blood pump within the descending aorta utilizing an arterial interface device having a vascular graft and stopper at the subclavian artery access.

47. A blood pump assembly comprising:
a balloon defining an elongated inflatable chamber, the balloon having a distal end and a proximal end, wherein:
the distal end is rounded,
the distal end and the elongated inflatable chamber are one-piece, and the proximal end has a cylindrical region including an opening; and an inflation tube coupled to the opening of the proximal end of the balloon via a coating layer disposed over a coupling site to affix the balloon to the inflation tube, the coating layer providing a smooth exterior profile to the coupling site so that an exterior surface of the assembly is configured to couple the balloon to the inflation tube and provide a smooth transition from the balloon to the inflation tube, and the inflation tube defining a fluid channel in fluid communication with the inflatable chamber;

wherein, between the distal end and the proximal end, the balloon has a central region having an elongated cylindrical shape when in an inflated state, and wherein a distalmost end of the inflation tube is coupled to the cylindrical region of the proximal end of the balloon such that the balloon has a substantially flat planar shape when in an uninflated state, the substantially flat planar shape and the coating layer being configured to promote laminar flow of fluid within a blood vessel in which the balloon is implanted when the balloon is in the uninflated state.

48. A blood pump assembly comprising:

a balloon defining an elongated inflatable chamber, the balloon having a distal end and a proximal end, wherein:

the distal end is rounded, the balloon lacks an interior support member, and the proximal end has a cylindrical region including an opening; and an inflation tube coupled to the opening of the proximal end of the balloon via a coating layer disposed over a coupling site to affix the balloon to the inflation tube, the coating layer providing a smooth exterior profile to the coupling site so that an exterior surface of the assembly is configured to couple the balloon to the inflation tube and provide a smooth transition from the balloon to the inflation tube, and the inflation tube defining a fluid channel in fluid communication with the inflatable chamber;

wherein, between the distal end and the proximal end, the balloon has a central region having an elongated cylindrical shape when in an inflated state, and wherein a distalmost end of the inflation tube is coupled to the cylindrical region of the proximal end of the balloon such that the balloon has a substantially flat planar shape when in an uninflated state, the substantially flat planar shape and the coating layer being configured to promote laminar flow of fluid within a blood vessel in which the balloon is implanted when the balloon is in the uninflated state.

49. A blood pump assembly comprising:

a balloon defining an elongated inflatable chamber, the balloon having distal end and a proximal end, wherein the distal end is rounded and the proximal end has a cylindrical region including an opening; and an inflation tube coupled to the opening of the proximal end of the balloon via a coating layer disposed over a coupling site to affix the balloon to the inflation tube, the coating layer providing a smooth exterior profile to the coupling site so that an exterior surface of the assembly is configured to couple the balloon to the inflation tube and provide a smooth transition from the balloon to the inflation tube, and the inflation tube defining a fluid channel in fluid communication with the inflatable chamber;

wherein, between the distal end and the proximal end, the balloon has a central region having an elongated cylindrical shape when in an inflated state, and wherein a distalmost end of the inflation tube is coupled to the cylindrical region of the proximal end of the balloon such that the balloon has a substantially flat planar shape when implanted in a blood vessel and in an uninflated state, the substantially flat planar shape and the coating layer being configured to promote laminar flow of fluid within the blood vessel in which the balloon is implanted when the balloon is in the uninflated state.

* * * * *